United States Patent
Yu et al.

(10) Patent No.: US 6,740,327 B2
(45) Date of Patent: *May 25, 2004

(54) OLIGOSACCHARIDE ALDONIC ACIDS AND THEIR TOPICAL USE

(76) Inventors: Ruey J. Yu, 4 Lindenwold Ave., Ambler, PA (US) 19002; Eugene J. Van Scott, 3 Hidden La., Abington, PA (US) 19001

(*) Notice: Subject to any disclaimer, the term of this patent is extended or adjusted under 35 U.S.C. 154(b) by 212 days.

This patent is subject to a terminal disclaimer.

(21) Appl. No.: 09/987,023

(22) Filed: Nov. 13, 2001

(65) Prior Publication Data

US 2002/0028227 A1 Mar. 7, 2002

Related U.S. Application Data

(63) Continuation of application No. 09/487,228, filed on Jan. 19, 2000, now Pat. No. 6,335,023.
(60) Provisional application No. 60/141,264, filed on Jun. 30, 1999.

(51) Int. Cl.[7] ............................ A61K 7/00; A61K 31/19
(52) U.S. Cl. ........................ 424/401; 424/400; 514/557
(58) Field of Search ............................... 424/400, 401; 514/557

(56) References Cited

U.S. PATENT DOCUMENTS

| | | |
|---|---|---|
| 1,772,975 A | 8/1930 | Wieland .................... 514/557 |
| 2,118,566 A | 5/1938 | De Wayne .................... 167/90 |
| 3,227,616 A | 1/1966 | Van Wessem et al. ......... 167/91 |
| 3,666,863 A | 5/1972 | Swanback .................... 424/316 |
| 3,689,668 A | 9/1972 | Piette ........................ 514/532 |
| 3,806,593 A | 4/1974 | Swanback et al. ............. 424/28 |
| 3,879,537 A | 4/1975 | Van Scott et al. ........... 424/311 |
| 3,920,835 A | 11/1975 | Van Scott et al. ........... 424/311 |
| 3,984,566 A | 10/1976 | Van Scott et al. ........... 424/283 |
| 3,988,470 A | 10/1976 | Van Scott et al. ........... 424/283 |
| 3,991,184 A | 11/1976 | Kludas et al. ............... 424/177 |
| 4,021,572 A | 5/1977 | Van Scott et al. ........... 424/317 |
| 4,053,630 A | 10/1977 | Yu et al. .................... 514/494 |
| 4,105,783 A | 8/1978 | YU et al. .................... 424/283 |
| 4,197,316 A | 4/1980 | Yu et al. .................... 424/283 |
| 4,234,599 A | 11/1980 | Van Scott et al. ........... 424/279 |
| 4,246,261 A | 1/1981 | Van Scott et al. ........... 424/240 |
| 4,287,214 A | 9/1981 | Van Scott et al. ........... 424/346 |
| 4,294,852 A | 10/1981 | Wildnauer et al. ........... 424/317 |
| 4,363,815 A | 12/1982 | YU et al. .................... 424/274 |
| 4,380,549 A | 4/1983 | Van Scott et al. ........... 424/317 |
| 4,507,319 A | 3/1985 | Barratt et al. ............... 514/546 |
| 4,518,789 A | 5/1985 | YU et al. .................... 560/105 |
| 4,608,370 A | 8/1986 | Aronsohn .................... 514/159 |
| 4,612,331 A | 9/1986 | Barrett et al. ............... 514/558 |
| 4,666,712 A | 5/1987 | Hollenberg et al. |
| 4,929,722 A | 5/1990 | Partain et al. ............... 536/20 |
| 4,983,382 A | 1/1991 | Wilmott et al. .............. 424/62 |
| 5,021,451 A | 6/1991 | McLane et al. ............... 514/460 |
| 5,091,171 A | 2/1992 | YU et al. .................... 514/349 |
| 5,093,109 A | 3/1992 | Mausner ....................... 424/63 |
| 5,108,751 A | 4/1992 | Hagan et al. ................ 424/401 |
| 5,153,230 A | 10/1992 | Jaffery ........................ 514/847 |
| 5,290,766 A | 3/1994 | Choong |
| 5,478,829 A | 12/1995 | Conrath |
| 5,554,597 A | 9/1996 | Yu et al. |
| 5,714,163 A | 2/1998 | Forssen et al. |
| 5,877,212 A | 3/1999 | Yu et al. |
| 6,335,023 B1 * | 1/2002 | Yu et al. ..................... 424/401 |

FOREIGN PATENT DOCUMENTS

| | | |
|---|---|---|
| AU | 64399 | 7/1975 |
| DE | 2517413 | 11/1975 |
| DE | 3540175 | 5/1987 |
| EP | 007 785 | 2/1980 |
| EP | 086 070 | 8/1983 |
| EP | 273202 | 9/1988 |
| EP | 413 528 | 2/1991 |
| EP | 508324 | 10/1992 |
| GB | 1316971 | 5/1973 |
| GB | 1337408 | 11/1973 |
| WO | 96/40047 | 12/1996 |
| ZA | 752066 | 4/1975 |

OTHER PUBLICATIONS

Webster's Ninth New Collegiate Dictionary, Merriam–Webster Inc. (1983) page 1272.

Derwent Abstract 86–064922[10] for JP 61–015810 (Jan. 23, 1986), Nonogawa, Shuji YG.

Sadik, F., O–T–C Products for Corns, Calluses, Warts *Journal of the American Pharmaceutical Association*, vol. NS10, No. 1, pp. 8–12 (1970).

Osipow, L.I., A Buffering Humectant for Cosmetics, *Drug and Cosmetic Industry*, vol. 88, No. 4, pp. 438–515 (1961).

Stern, E.C., Topical Application of Lactic Acid in the Treatment and Prevention of Certain Disorders of the Skin, *The Urologic and Cutaneous Review*, vol. 50, No. 2, pp. 106–107 (1946).

Darr, D., Topical Vitamin C Protects the Skin from Ultraviolet Radiation–Induced Damage, *British Journal of Dermatology*, vol. 127, pp. 247–253 (1992).

(List continued on next page.)

*Primary Examiner*—Shelley A. Dodson
(74) *Attorney, Agent, or Firm*—Hunton & Williams

(57) ABSTRACT

Compositions comprising oligosaccharide aldonic acids are useful for general care, as well as for treatment and prevention, of various cosmetic conditions and dermatological disorders, including those associated with intrinsic and/or extrinsic aging, as well as with changes or damage caused by extrinsic factors; general care, as well as treatment and prevention of diseases and conditions, of the oral, and vaginal mucosa; for general oral care, as well as treatment and prevention of oral and gum diseases; and for wound healing of the skin. Compositions comprising oligosaccharide aldonic acids may further comprise a cosmetic, pharmaceutical or other topical agent to enhance or create synergetic effects.

48 Claims, No Drawings

OTHER PUBLICATIONS

Aggarwal, R.R., et al., A Clinical Trial With Cotaryl Cream in Hyperkerototic Skin Conditions, *Indian J. Dermatol. Venerbol.*, vol. 45, No. 6, pp. 442–444.

Kligman et al., "The Anatomy and Pathogenesis of Wrinkles," *British Journal of Dermatology*, 113, pp. 37–42 (1985).

Grove et al., "Age–Associated Changes in Human Epidermal Cell Renewal," *Journal of Gerontology*, 38 No. 2, pp. 137–142 (1983).

Derwent Abstract 85–228562[37]for SU 1140785 (Feb. 23, 1985), Gerchikov, et al.

Chemical Abstracts 70:14330q for French patent 1,505,552 (1967), Durafrourd.

Chemical Abstracts 85:25286r for DE 2,462,221 (1976), Hadhary, et al.

Chemical Abstracts 108:210190m (1988).

*Dorland's Medical Dictionary*, 26$^{th}$ Ed., Saunders, Philadelphia, PA (1981) 647, 696–97.

Neostrata Company Notice (1992).

Merck Index, 10$^{th}$ Ed., Rathway, New Jersey, (1983) p. 768.

Weiss, J. S., M. D., et al., "Topical Tretinoin in the Treatment of Aging Skin" *J. Amer. Acad. of Dermatology*, vol. 19 (1988) pp. 169–175.

Weiss, J. S., M.D., et al., "Topical Tretinoin Improves Photoaged Skin: A Double–blind Vehicle Controlled Study", *J. Amer. Medical Assn.*, vol. 259, No. 4 (1988) pp. 527–532.

Moisturizing & Emolliency Documentary, Unusual Moisturizers and Emollients: Patent Digest for 1966–1977, Cosmetics and Toiletries, vol. 93, Apr. 1978, pp. 55–60.

Chemical Abstracts 79710x, Juhlin, L.A., Dermatologically Useful Composition, vol. 84 (1976).

Fredriksson, T. et al., Urea Creams in the Treatment of Dry Skin and Hand Dermatitis, *Pharmacology and Therapeutics*, pp. 442–444 (1975).

Blair, C., The Action of a Urea–Lactic Acid Ointment in Ichthyosis, *British Journal of Dermatology* vol. 94 pp. 145–153 (1976).

Van Scott et al., Control of Keratinization with α–Hydroxyacids and Related Compounds, *Arch Dermatol* vol. 110 pp. 586–590 (1974).

Grice, K., et al., Urea and Retinoic Acid in Ichthyosis and Their Effect on Transepidermal Water Loss and Water Holding Capacity of Stratum Conneum, *Acta Dermatovener* vol. 53 pp. 114–118 (1973).

Harry, R. G., The Principles and Practice of Modern Cosmetics, 6$^{th}$ Ed., Chapters 6 and 39, (1973).

Lavker et al., "Changes in Skin Surface Patterns With Age," *Journal of Gerontology*, 35, No. 2 , pp 348–354 (1980).

Goldenberg, R.L., et al., Correlation of Skin Feel of Emollients to Their Chemical Structure, *J. Soc. Cosmet. Chem.*, vol. 22 pp. 635–654 (1971).

Hunt et al., "Anaerobic Metabolism and Wound healing . . .", *The American Journal of Surgery*, 135: pp. 328–332 (1978).

Cornstock, et al., "Effect of Lactate on Collagen Proline . . .," *Proceedings of the National Academy of Science*, 66: No. 2, pp. 552–557 (1970).

Terry et al., "Implications of Heavy Chain Disease . . .," *Proceedings of the National Academy of Science*, 66: No. 2, pp. 558–563 (1970).

Cimino et al., "Ability of Nonenzymic Nitration or . . .," *Proceedings of the National Academy of Science*, 66: No. 2, pp. 564–571 (1970).

Chemical Abstracts No. 85:25286r, Chemical Abstracts, No. 4, p. 248, (1976).

Szorcsik et al., D–Lactobionic Acid Complexes with Cesium(1), Aluminum(III) and Iron (III), *Biocoordination Chemistry Research Group of Hungarian Academy of Sciences; Department of Chemistry University of Bergen, Department of Inorganic and Analytical Chemistry, A. Jozsef University Hungary*; Specification 98: Abstracts 1p.

Irwin et al, Calculation of Immobilized Glucose Oxidase Bimolecular Reaction Progress Curves Utilizing a Nested and Numerically–Integrated Ordered–Sequential (Ping–Pong) Rate Expression, *Agricultural Research Service*, Jul. 29, 1996, 1p.

Hunt et al., Anaerobic Metabolism and Would Healing: An Hypothesis for the Initiation and Cessation of Collagen Syntheses in Wounds, *The American Journal of Surgery*, Mar. 1978, pp. 328–332.

Comstock et al., Effect of Lactate on Collagen Proline Hydroxylase Activity in Cultured L–929 Fibroblasts; *National Academy of Sciences*, vol. 66, No. 2, pp. 552–557, Jun. 1970.

Terry et al., Implications of Heavy Chain Disease Protein Sequences for Multiple Gene Theories of Immunoglobulin Syntheses, *National Academy of Sciences*, vol. 66, No. 2, pp. 558–563, Jun. 1970.

Cimino et al., Ability of Nonenzymic Nitration or Acetylation of E. coli Glutamine Synthetase to Produce Effects Analogous to Enzymic Adenylylation, *National Acedemy of Sciences*, vol, 66, No. 2 pp. 564–571, Jun. 1970.

Irwin et al., Calculation of Immobilized Glucose Oxidase Bimolecular . . .,*Agricultural Research Service*, 1pp., Jul. 1996.

Szorciski et al., D–Lactobionic Acid Complexes with Cesium(1), Aluminum(III) and Iron(III), *Hungarian Academy of Sciences*, Specification 98; Abstracts, 1pp.

\* cited by examiner

OLIGOSACCHARIDE ALDONIC ACIDS AND THEIR TOPICAL USE

This application is a continuation of Ser. No. 09/487,228 filed on Jan. 19, 2000, now U.S. Pat. No. 6,335,023B1 which claims the benefit of U.S. provisional application Serial No. 60/141,264, filed Jun. 30, 1999.

FIELD OF THE INVENTION

This application relates to compositions comprising oligosaccharide aldonic acids and related compounds, and their use for cosmetic and dermatological indications, reducing and soothing mucosa and skin erythema, inflammation or reaction caused by internal or external factors, wound healing, and care of skin, hair, nail, and oral and vaginal mucosa, including the use for changes associated with intrinsic and extrinsic aging, and changes or damage caused by extrinsic factors such as sunlight, radiation, air pollution, wind, cold, heat, dampness, chemicals, smoke, and cigarette smoking.

BRIEF DESCRIPTION OF THE PRIOR ART

In our U.S. patent application Ser. No. 06/945,680, filed Dec. 23, 1986, entitled "Additives Enhancing Topical Actions of Therapeutic Agents, " and related applications, issuing, inter alia, as U.S. Pat. Nos. 5,665,776, 5,389,677, and 5,422,370, we described and claimed compositions for and methods of enhancing the therapeutic effect of a cosmetic or pharmaceutical agent by using a hydroxyacid in combination with the agent. The generic structure of hydroxymonocarboxylic acids disclosed may appear similar to the one described herein for oligosaccharaide aldonic acids. The location of the $R_2$ molecule is a notable difference. This application disclosed that "when n=0 and m=1 or more, the hydroxymonocarboxylic acid is also called aldonic acid. The name comes from a carbohydrate, aldose, which may be oxidized to aldonic acid by the oxidation of the aldehyde group in aldose to the carboxylic group." The application, however, does not disclose or suggest that a carbohydrate may be chemically linked to an aldonic acid. Thus, this application does not disclose or suggest oligosaccharide aldonic acids.

In our related U.S. patent application Ser. No. 07/683,437, filed Apr. 10, 1991, entitled "Compositions Comprising 2-Hydroxycarboxylic Acids and Related Compounds, and Methods for Alleviating the Signs of Dermatological Aging," and related applications, and issuing, inter alia, as U.S. Pat. Nos. 5,547,988, 5,554,597, and 5,561,158, we described and claimed the use of topical compositions containing a 2-hydroxycarboxylic acid or related compound for use in alleviating or improving the signs of aging, including the signs caused by intrinsic and extrinsic aging or extrinsic factors, of the skin, hair and nails. Among the many compounds disclosed in this application, lactobionic acid, an oligosaccharide aldonic acid, is listed as a useful related compound.

We have now discovered that oligosaccharide aldonic acids and related compounds, as a group, provide numerous benefits in the treatment and prevention of various cosmetic conditions and dermatological disorders, including those associated with intrinsic and extrinsic aging, as well as changes and damage caused by extrinsic factors. Oligosaccharide aldonic acids and related compounds also provide numerous benefits in the treatment of skin wounds; reducing or soothing erythema, inflammation or irritation; general care, as well as treatment and prevention of diseases and conditions, of the nasal, oral and vaginal mucosa; and general oral care and treatment and prevention of oral and gum diseases.

We have further discovered that oligosaccharide aldonic acids possess unexpected physicochemical properties, including binding with water and the formation of a gel matrix with water. In addition, the oligosaccharaide aldonic acids disclosed herein are antioxidant substances. Moreover, beneficial effects from an oligosaccharaide aldonic acid within the skin, nail and hair are expected to include those provided by glycosaminoglycans (GAGs). This is due to similarities in the basic chemical structure of oligosaccharaide aldonic acids and GAGs, and the fact that they both form a gel matrix with water. Exemplary beneficial effects and functions of GAGs inside the skin includes (i) binding with polycations and cations, such as sodium and potassium ions, to enhance water retention, and (ii) specific interaction with collagen, elastin, fibronectin, laminin and other proteins to stabilize the turgor of the skin.

SUMMARY OF THE INVENTION

Accordingly, it is an object of this invention to provide methods and compositions which are useful in the treatment and prevention of certain cosmetic conditions and dermatological disorders, promote wound healing, and are useful for general care of skin, hair, nail, oral and vaginal mucosa, and oral and gum diseases.

We have now discovered that oligosaccharide aldonic acids have protective as well as healing effects for skin, hair, nail; oral, nasal and vaginal mucosa. The oligosaccharide aldonic acids include glycerbionic acids, erythrobionic acids, threobionic acids, ribobionic acids, arabinobionic acids, xylobionic acids, lyxobionic acids, allobionic acids, altrobionic acids, glucobionic acids, mannobionic acids, gulobionic acids, idobionic acids, galactobionic acids, talobionic acids, alloheptobionic acids, altroheptobionic acids, glucoheptobionic acids, mannoheptobionic acids, guloheptobionic acids, idoheptobionic acids, galactoheptobionic acids and taloheptobionic acids.

Compositions comprising oligosaccharide aldonic acids are beneficial and effective for general care, reducing and soothing mucosa and skin erythema, inflammation or reaction caused by internal or external factors, treatment and healing of skin, hair, nail; nasal, oral and vaginal mucosa including treatment, healing and prevention of cosmetic conditions and dermatological indications as well as cosmetic and clinical signs of changes associated with intrinsic aging, or the damages caused by extrinsic factors as sunlight, radiations, air pollution, wind, cold, dampness, heat, chemicals, smoke, and cigarette smoking.

General care, reducing and soothing mucosa and skin erythema, inflammation or irritation caused by internal or external factors, treatment and healing of skin, hair, nail; nasal, oral and vaginal mucosa, and treatment, healing and prevention of cosmetic conditions and dermatological indications as well as cosmetic and clinical signs of changes associated with intrinsic aging, or the damages caused by extrinsic factors as sunlight, radiations, air pollution, wind, cold, dampness, heat, chemicals, smoke, and cigarette smoking may include blemished, irritated, inflamed, unhealthy, damaged or abnormal mucosa, skin, hair, nail, nostril, ear canal or vaginal conditions; oral or gum disease; disturbed keratinization; defective syntheses or repair of dermal components, and changes associated with intrinsic and extrinsic aging of skin, nail and hair. Those conditions and indications include dryness of the skin, nail and hair; xerosis; ichthyosis; palmar and plantar hyperkeratoses; uneven and rough surface of skin, nail and hair; dandruff; Darier's disease; lichen simplex chronicus; keratoses; acne; pseudofolliculitis barbae; eczema; psoriasis; pruritus; warts; herpes; age spots; lentigines; melasmas; blemished skin; mottled skin; hyperkeratoses; hyperpigmented skin; abnormal or diminished syntheses of collagen, glycosaminoglycans, proteoglycans and elastin as well as diminished levels of such components in the dermis; cellulite; stretch marks; skin lines; fine lines; wrinkles; thinning of skin, nail plate and hair; skin thickening due to elastosis of photoaging, loss or reduction of skin, nail and hair resiliency, elasticity and recoilability; lack of skin, nail and hair lubricants and luster; dull and older-looking skin, nail and hair; fragility and splitting of nail and hair.

Oligosaccharide aldonic acids are also beneficial for wound healing of skin; irritated or inflamed mucosa or skin; for skin lightening; for cleansing of skin, hair and nail; for conditioning of skin and nail; for protection from extrinsic factors; for mouthwashes; for use as antioxidant agent, toner, cleanser, moisturizer, emollient, protectant, foundation makeup, beauty masks, face powders, rouge, cover up, lipsticks, eye makeup, dentifrices, mouthwashes, suntan preparation, soap preparation, and other topical preparations.

DETAILED DESCRIPTION OF THE PREFERRED EMBODIMENTS

1. Oligosaccharaide Aldonic Acids and Related Compounds

An oligosaccharide aldonic acid may be defined as an aldonic acid having a carbohydrate chemically linked to the aldonic acid. The total number of carbohydrate monomers including the aldonic acid itself ranges from 2 to 10. The aldonic acid may be described as an oxidized form of a carbohydrate. For example, gluconic acid may be obtained from glucose through an oxidation of the aldehyde group to a carboxylic group. Although an oligosaccharide aldonic acid may consist of one to ten aldonic acid units, preferred compounds contain one aldonic acid unit and one to nine carbohydrate monomers. When the total number of the carbohydrate monomers including the aldonic acid itself are 2, 3, 4, 5, 6, 7, 8, 9 and 10, these oligosaccharide aldonic acids may be respectively called aldobionic acid, aldotrionic acid, aldotetraonic acid, aldopentaonic acid, aldohexaonic acid, aldoheptaonic acid, aldooctaonic acid, aldononaonic acid and aldodecaonic acid. The most preferred is aldobionic acid. If the name of a precursor oligosaccharide is known, such name may be utilized as a prefix. For example, lactobionic acid is derived from lactose, maltobionic acid from maltose, cellobionic acid from cellobiose, isomaltobionic acid from isomaltose, gentiobionic acid from gentiobiose and laminarabionic acid from laminarabiose. Alternatively, the name of a specific aldonic acid may also be used such as glycerbionic acid, erythrobionic acid, xylobionic acid, mannobionic acid and glucoheptabionic acid.

The smallest aldonic acid having three carbon atoms is glyceric acid, which is obtained from glyceraldehyde. A carbohydrate having one to nine monomers may be chemically linked to one of the two hydroxyl groups at 2nd or 3rd carbon position of glyceric acid to form an oligosaccharide aldonic acid. When one carbohydrate monomer is linked to glyceric acid the compound may be called glycerbionic acid.

Erythronic acid and threonic acid, which have four carbon atoms, may be obtained respectively from erythrose and threose through an oxidation process. A carbohydrate having one to nine monomers may be chemically linked to one of the three hydroxyl groups at 2nd, 3rd or 4th carbon position of the aldonic acid. When one carbohydrate monomer is attached to the aldonic acid the resulting compound may be called erythrobionic acid or threobionic acid.

Ribonic acid, arabinoic acid, xylonic acid and lyxonic acid, which have five carbon atoms, may be obtained respectively from ribose, arabinose, xylose and lyxose through an oxidation process. A carbohydrate having one to nine monomers may be chemically linked to one of the four hydroxyl groups at 2nd, 3rd, 4th or 5th carbon position of the aldonic acid. When one carbohydrate monomer is attached to the aldonic acid, the resulting compound may be called ribobionic acid, arabinobionic acid, xylobionic acid or lyxobionic acid.

Allonic acid, altronic acid, gluconic acid, mannonic acid, gulonic acid, idonic acid, galactonic acid and talonic acid, which have six carbon atoms, may be obtained respectively from allose, altrose, glucose, mannose, gulose, idose, galactose and talose through oxidation. A carbohydrate having one to nine monomers may be chemically linked to one of the five hydroxyl groups at 2nd, 3rd, 4th, 5th or 6th carbon position of the aldonic acid. When one carbohydrate monomer is attached to the aldonic acid, the resulting compound may be called allobionic acid, altrobionic acid, glucobionic acid, mannobionic acid, gulobionic acid, idobionic acid, galactobionic acid or talobionic acid.

Alloheptonic acid, altroheptonic acid, glucoheptonic acid, mannoheptonic acid, guloheptonic acid, idoheptonic acid, galactoheptonic acid and taloheptonic acid, which have seven carbon atoms, may be obtained respectively from alloheptose, altroheptose, glucoheptose, mannoheptose, guloheptose, idoheptose, galactoheptose and taloheptose through oxidation. A carbohydrate having one to nine monomers may be chemically linked to one of the six hydroxyl groups at 2nd, 3rd, 4th, 5th, 6th or 7th carbon position of the aldonic acid. When one carbohydrate monomer is attached to the aldonic acid, the resulting compound may be called alloheptobionic acid, altroheptobionic acid, glucoheptobionic acid, mannoheptobionic acid, guloheptobionic acid, idoheptobionic acid, galactoheptobionic acid or taloheptobionic acid.

A common carbohydrate monomer such as glucose contains an aldehyde group (first carbon position) and five hydroxyl groups, whereas fructose contains a keto group (at second carbon position) and five hydroxyl groups. Many carbohydrate monomers form a five (furanoside) or six (pyranoside) member ring between the aldehyde or keto group and one of the hydroxyl groups at 4th or 5th carbon position of the molecule. A newly formed hydroxyl group (anomeric hydroxyl) at the original functional group has two isomers: alpha or beta anomer, depending on down or up of the hydroxyl position. A disaccharide is usually formed from two monosaccharides (carbohydrate monomers) by eliminating one mole of water between two anomeric hydroxyl groups (non-reducing disaccharide) or between one anomeric hydroxyl of the second monomer and one of the hydroxyl in the first monomer (reducing disaccharide). A non-reducing disaccharide such as sucrose formed from fructose and glucose can not be oxidized to an aldonic acid, whereas a reducing disaccharide such as maltose formed from two glucose molecules can be oxidized to maltobionic acid. Oligosaccharides containing three to ten monomers may be formed in the same manner as in that of disaccharides. As an alternative example, tetrasaccharides may also be formed from two disaccharides.

Since the chemical link between two carbohydrate monomers can be at different carbon positions, numerous different oligosaccharides may be formed. The same is true for oligosaccharide aldonic acids. For example, the disaccharides maltose and cellobiose are both formed from two glucose molecules linked between the anomeric hydroxyl of the second glucose and the hydroxyl at the $4^{th}$ carbon position of the first glucose molecule. The only difference is that maltose is an alpha anomer and cellobiose is a beta anomer. The same is true when these two disaccharides are oxidized to aldonic acids. The only difference between maltobionic acid and cellobionic acid is that the former is an alpha and the latter is a beta anomer.

Many disaccharides which may be converted to bionic acids include glycerbioses, erythrobioses, threobioses, ribobioses, arabinobioses, xylobioses, lyxobioses, allobioses, altrobioses, glucobioses, mannobioses, gulobioses, idobioses, galactobioses, talobioses, alloheptobioses, altroheptobioses, glucoheptobioses, mannoheptobioses, guloheptobioses, idoheptobioses, galactoheptobioses, taloheptobioses, maltose, isomaltose, lactose, cellobiose, gentiobiose, laminaribiose, kojibiose, melibiose, nigerose, rutinose and sophorose. Bionic acids may be obtained from these disaccharides by an oxidation process with hypoiodite, bromine water or enzyme.

In accordance with the present invention, the generic structure of oligosaccharide aldonic acids may be represented as follows:

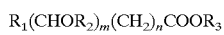

wherein:

$R_1$ and $R_3$ are independently H or an alkyl, aralkyl or aryl group of saturated or unsaturated, straight or branched chain or cyclic form, having 1 to 25 carbon atoms;

m is 2, 3, 4, 5, 6, 7, 8, 9, 10 or 11;

n is 0, 1, 2, 3, 4, 5, 6, 7, 8, or 9;

$R_2$ is independently selected from H or any carbohydrate having from 1 to 9 monomers in each ($CHOR_2$), and at least one $R_2$ is a carbohydrate. For example, when m=5, one of the five $R_2$ may be a carbohydrate and the remaining four $R_2$ may be H;

H attached to carbon atom may be substituted by I, F, Cl, Br, $NH_2$, $NHCOCH_3$, SH, or alyl, alkoxyl, aralkyl or aryl group of saturated or unsaturated, straight or branched chain or cyclic form, having from 1 to 9 carbon atoms;

$R_1$, $R_2$, $OR_2$ or H may carry or be substituted with CHO, COOH, sulfate, phosphate, nitrate, or lower alkoxyl having from 1 to 5 carbon atoms;

H of the OH group may be substituted by an acyl group having from 2 to 25 carbon atoms, such as acetyl ($CH_3CO$), propanoyl ($CH_3CH_2CO$), octanoyl [$CH_3(CH_2)_6CO$], octadecanoyl [$CH_3(CH_2)_{16}CO$], eicosanoyl [$CH_3(CH_2)_{18}CO$], tetraeicosanoyl [$CH_3(CH_2)_{22}CO$] or benzoyl ($C_6H_5CO$) group.

Oligosaccharide aldonic acids according to the present invention may be present as isomeric D, L, DL or any other isomeric or non-isomeric form, saturated or unsaturated, straight or branched chain or cyclic form, free acid, ester, lactone, salt or partial salt form with organic or inorganic alkali.

The preferred oligosaccharide aldonic acids contain 2 to 6 carbohydrate monomers, and more preferred ones contain 2 to 3 carbohydrate monomers, and the most preferred oligosaccharide aldonic acids contain two carbohydrate monomers. The most preferred oligosaccharide aldonic acids may be called bionic acids which contain two carbohydrate monomers. In the bionic acid, the chemical link between the two carbohydrate monomers can be at any carbon position. The preferred link is between the anomeric carbon of the second monomer chemically bond to any position other than the first carbon position of the first monomer. In addition, two anomeric isomers such as alpha and beta isomers can be formed when the second monomer is linked to the first monomer, and therefore numerous different bionic acids may exist. For example, glucobionic acids include maltobionic acid and cellobionic acid.

As an example, chemical structures of some oligosaccharaide aldonic acids are depicted below:

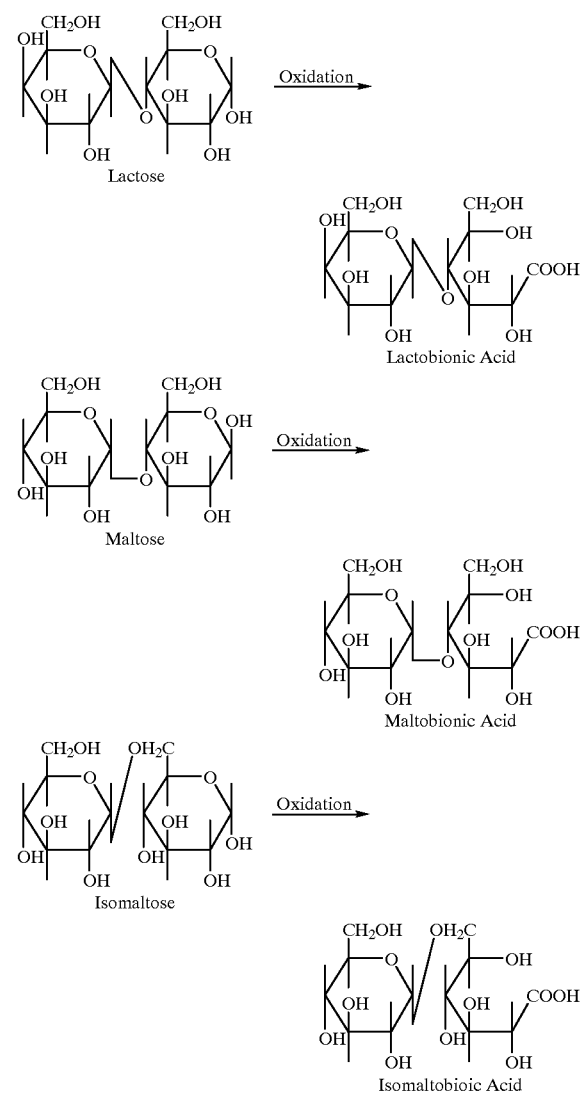

Oligosaccharide aldonic acid lactones are usually obtained from their aldonic acids by eliminating one mole of water through intramolecular cyclization between the carboxyl group and one of the hydroxyl groups. Common lactones consist of five or six member rings.

Examples of lactone form include lactobionolactone, maltobionolactone, isomaltobionolactone, cellobionolactone, chitobionolactone, gentiobionolactone, glucobionolactone, galactobionolactone, mannobionolactone, ribobionolactone, kojibionolactone, xylobionolactone, arabinobionolactone, nigerobionolactone, laminarabinobionolactone, maltotrionolactone, isomaltotrionolactone, chitotrionolactone, cellotrionolactone, gentiotrionolactone, maltotetraonolactone, cellotetraonolactone and chitotetraonolactone.

Examples of ester form include methyl lactobionate, ethyl lactobionate, propyl lactobionate, benzyl lactobionate, methyl maltobionate, ethyl maltobionate, propyl maltobionate, benzyl maltobionate, methyl cellobionate, ethyl cellobionate, propyl cellobionate and benzyl cellobionate.

Examples of acyl form include acetyl lactobionic acid, acetyl maltobionic acid and acetyl cellobionic acid.

Examples of both acyl and ester form include acetyl lactobionic acid methyl, ethyl or propyl ester; acetyl maltobionic acid methyl, ethyl or propyl ester; acetyl cellobionic acid methyl, ethyl or propyl ester.

On one embodiment of the inventions, the group of oligosaccharide aldonic acids and related compounds according to the invention are the group of compounds discussed herein, but excluding lactobionic acid. In another embodiment of the invention the group of oligosaccharide aldonic acids and related compounds according to the invention are the group of compounds discussed herein, but excluding lactobionic acid and salts, lactones, and thereof.

Oligosaccharide aldonic acids may be classified into groups according the number of carbohydrate monomers such as aldobionic acid, aldotrionic acid, aldotetraonic acid, aldopentaonic acid, aldohexaonic acid, aldoheptaonic acid, aldooctaonic acid, aldononaonic acid and aldodecaonic acid. The preferred groups are aldobionic acid up to aldohexaonic acid, with more preferred groups of aldobionic acid up to aldotetraonic acid, and with most preferred groups being aldobionic acid and aldotrionic acid.

Many different aldobionic acids and aldotrionic acids exist due to various carbohydrate monomers and different linking positions between two monomers. For example, even in the smallest molecule of glycerbionic acid (six carbon atoms) formed from glyceraldehyde (second monomer) and glyceric acid, there are two different glycerbionic acids; linking at 2nd or 3rd carbon position of the glyceric acid. Glycerbionic acids also include various second monomers linked to glyceric acid at the 2nd or 3rd carbon position. The second monomers include erythrose, threose, ribose, arabinose, xylose, lyxose, allose, altrose, glucose, mannose, gulose, idose, galactose, talose, 6-deoxymannose, 2-deoxyaminoglucose and fucose. Some representative oligosaccharide aldonic acids include the following:

(i) Aldobionic Acids (Bionic Acids)

These bionic acids consist of one carbohydrate monomer linked to an aldonic acid, and include glycerbionic acids, erythrobionic acids, threobionic acids, ribobionic acids, arabinobionic acids, xylobionic acids, lyxobionic acids, allobionic acids, altrobionic acids, glucobionic acids, mannobionic acids, gulobionic acids, idobionic acids, galactobionic acids, talobionic acids, alloheptobionic acids, altroheptobionic acids, glucoheptobionic acids, mannoheptobionic acids, guloheptobionic acids, idoheptobionic acids, galactoheptobionic acids, taloheptobionic acids, chitobionic acids, hyalobiouronic acids, hyalourobionic acids, chondrosines, chondrosinbionic acids, cellobiouronic acids, and cellourobionic acids.

As an example, glucobionic acids include lactobionic acid, isolactobionic acid, maltobionic acid, isomaltobionic acid, cellobionic acid, gentiobionic acid and laminarabionic acid. All these bionic acids are formed from the same or a different carbohydrate monomer linked to gluconic acid through a different or the same position. Other individually named bionic acids include melibionic acid, nigerobionic acid, rutinobionic acid, sophorobionic acid and kojibionic acid.

(ii) Aldotrionic Acids (Trionic Acids)

These trionic acids consist of two carbohydrate monomers linked jointly or separately to an aldonic acid, and include glycertrionic acids, erythrotrionic acids, threotrionic acids, ribotrionic acids, arabinotrionic acids, xylotrionic acids, lyxotrionic acids, allotrionic acids, altrotrionic acids, glucotrionic acids, mannotrionic acids, gulotrionic acids, idotrionic acids, galactotrionic acids, talotrionic acids, alloheptotrionic acids, altroheptotrionic acids, glucoheptotrionic acids, mannoheptotrionic acids, guloheptotrionic acids, idoheptotrionic acids, galactoheptotrionic acids, taloheptotrionic acids, chitotrionic acids, hyalotriouronic acids, hyalourotrionic acids, chondrosintrionic acids, cellotriouronic acids and cellourotrionic acids.

(iii) Other Oligosaccharide Aldonic Acids and Related Compounds

Aldonic acids with higher molecular weight may consist of three to nine carbohydrate monomers linked jointly or separately to an aldonic acid, and include aldotetraonic acids, aldopentaonic acids, aldohexaonic acids, aldoheptaonic acids, aldooctaonic acids, aldononaonic acids and aldodecaonic acids. Miscellaneous or related aldonic acids include those which are not readily represented or included in the above generic structure, or which have additional functional groups in the molecules, such as a carbohydrate linked to an uronic acid, which may or may not be represented by the above generic structure. A sulfate, phosphate, nitrate group, amino, acetamino group etc. may be substituted at H or OH similar to that of chitin, chitosan, hyaluronic acid, chodroitin sulfate, heparin, etc. to form substituted oligosaccharide aldonic acids.

2. Topical Uses of Oligosaccharide Aldonic Acids and Related Compounds (i) Oligosaccharide Aldonic Acids and Related Compounds Compositions comprising an oligosaccharide aldonic acid or related compound described herein have numerous beneficial effects and a broad range of uses. These compositions can comprise one or more than one oligosaccharide aldonic acid or related compound.

According to one aspect of the invention, these compositions may be used for general care; moisturizing; dry skin; reducing irritation or inflammation of or soothing skin and mucosa or treatment or prevention of skin or mucosa irritation or inflammation caused by external factors, such as chemicals; skin smoothing and itchy skin; as well as for treatment and prevention, of various cosmetic conditions and dermatological disorders, including those associated with intrinsic and/or extrinsic aging, as well as with changes or damage caused by extrinsic factors. In a preferred embodiment, the compositions may be used for skin, hair and nail changes associated with intrinsic and/or extrinsic aging, and changes or damage caused by extrinsic factors such as sunlight, radiations, air pollution, wind, cold, dampness, heat, chemicals, smoke, and cigarette smoking. In addition, the compositions of the present invention may be used to treat skin wounds, for example in aiding the healing of skin cuts, tears, lacerations, burns, punctures, and other wounds.

According to another aspect of the invention, these compositions may be used for general care, as well as treatment and prevention of diseases and conditions, of the oral, nasal and vaginal mucosa. For example, the compositions may be used for care and treatment of blemished, unhealthy, damaged, irritated, or abnormal oral, nasal or vaginal mucosa, and gum diseases.

According to still another aspect of the invention, these composition may be used for general oral care, as well as treatment and prevention of oral and gum diseases.

With respect to age associated skin changes, the underlying bases of these changes is described in U.S. Pat. No. 4,603,146 (Kligman). In particular, the underlying causes of skin changes associated with aging can be more easily understood in view of the following summary of the changes in the epidermis and dermis as aging progresses.

With increasing age and exposure of human to sun and other environmental traumas, cells divide at a slower rate (decreased capacity to renew themselves). They show marked irregularities in size, shape and staining properties; orderliness (polarity) from below to above is lost. The thickness of the epidermis decreases (atrophy). The horny layer which comprises the barrier against water loss and penetration of chemicals becomes abnormal due to the shedding (exfoliation) of cells in large group or clusters instead of as individual cells, resulting in roughness, scaling and dryness. There is loss of the orderly transformation of living epithelial cells into cornified dead cells which are shed at the surface, that is, differentiation is impaired. Aberrant differentiation results in numerous foci of abnormal epithelial growths or tumors, the most frequent and important of which are actinic keratoses. After many years these can transform into frank skin cancers called basal cell and squamous cell cancers. Pigment producing cells (melanocytes) can also become altered forming flat, dark growths (lentigo melanoma) which may progress to malignant melanoms.

The cells which make the fibers of the dermis become smaller and sparser with increasing age, usually in sun-damaged facial skin. There is a great loss of collagen fibers resulting in looseness and easy stretchability of the skin; elastic fibers become abnormal so that the skin does not promptly snap back after being stretched. Since the fibrous components comprise more than 90% of the bulk of skin of which 95% is collagen, the degradation of these fibers, especially collagen, is mainly responsible for wrinkling, laxness and loss of elasticity.

Additionally, small blood vessels become thin walled, dilated and often ruptured. Vascular supply thereby becomes compromised.

The signs of nail and hair changes associated with intrinsic aging and the damages caused by extrinsic factors include thinning of hair and nail plate; lack of lubricants and luster, and uneven surface of hair and nails; fragility and splitting of hair and nails; and reduction of flexibility, resiliency, and elasticity of hair and nails.

The conventional management of signs of aging skin has been the use of cosmetics, as well as medical procedures such as phenol, trichloroacetic acid, and other chemical peels, and plastic surgery, etc. Such medical procedures are costly and risky with serious side effects, and the treatments alter only the cosmetic appearance of the skin, without any significant modifications of the underlying aging process.

Topical application to the skin, hair or nails of a composition of the present invention is beneficial for various cosmetic conditions and dermatological disorders including those associated with intrinsic and/or extrinsic aging and extrinsic factors, and also including those characterized by the foregoing changes to the skin, hair and nails. Exemplary indications are characterized as disturbed keratinization, defective syntheses of dermal components, and changes associated with aging of skin, nail and hair; and those indications which include dryness or loose of skin, nail and hair; xerosis; ichthyosis; palmar and plantar hyperkeratoses; uneven and rough surface of skin, nail and hair; dandruff; Darier's disease; lichen simplex chronicus; keratoses; acne; pseudofolliculitis barbae; irritation; dermatoses; eczema; psoriasis; itchy scalp and skin; pruritus; warts; herpes; age spots; lentigines; melasmas; blemished skin; mottled skin; hyperkeratoses; hyperpigmented skin; abnormal or diminished syntheses of collagen, glycosaminoglycans, proteoglycans and elastin as well as diminished levels of such components in the dermis; stretch marks; skin lines; fine lines; wrinkles; thinning of skin, nail plate and hair; skin thickening due to elastosis of photoaging, loss or reduction of skin, nail and hair resiliency, elasticity and recoilability; lack of skin, nail and hair lubricants and luster; dull and older-looking skin, nail and hair; fragility and splitting of nail and hair; and other topical conditions and indications.

(ii) Combination Compositions

In addition, compositions comprising one or more than one oligosaccharide aldonic acid or related compound may also be incorporated into a composition comprising a cosmetic, pharmaceutical or other topical agent to enhance or create synergetic effects.

In accordance with this aspect of the invention, the compositions of the present invention may contain one or more oligosaccharide aldonic acids or related compounds to magnify the therapeutic effect of an unrelated cosmetic or pharmaceutical agent. At least one compound selected from the group consisting of oligosaccaride aldonic acids and related compounds may be incorporated into composition containing a cosmetic or pharmaceutical agent for any of the uses described above. It has been found that such incorporation results in magnified therapeutic efficacies which are not simply additive effects.

Most pharmaceutical drugs produce their therapeutic effects by first interacting with their receptors in the target tissues. Many drug receptors are functional macromolecules such as enzymes, cell membrane components or certain components of cells. The binding affinity or interacting property of a drug toward its specific receptor molecule is intimately governed by the chemical structure of the drug. Since most pharmaceutical agents are chemically different from oligosaccaride aldonic acids and related compounds of the instant invention, the respective receptor molecule should be different and so are the pharmacological actions and the therapeutic effects. Under such conditions if an oligosaccharide aldonic acid and/or related compound is incorporated into a composition containing a pharmaceutical agent, one of the following two consequences may arise:

(a) No enhancement or any substantial changes in either effect. In this case, the overall clinical effect would be a mixed effect, i.e. the effect due to the pharmaceutical agent alone mixed with the effect due to the oligosaccharide aldonic acid and/or related compound alone. Also in this case, the interaction between the pharmaceutical agent and its receptor molecule is not affected nor interfered by the presence of oligosaccharide aldonic acid and/or related compound. Nor does the oligosaccharide aldonic acid and/or related compound assist in or enhance the binding affinity or the interaction of the pharmaceutical agent toward its receptor molecule. The clinical results from such combination composition would be just the mixed effects.

(b) Amplified therapeutic action or substantial loss of therapeutic action in either effect. In this case, the interaction between the pharmaceutical agent and its receptor molecule is affected either positively or negatively by the presence of an oligosaccharide aldonic acid and/or related compound.

From the point of positive effect, the oligosaccharide aldonic acid and/or related compound may produce an amplified effect by either increasing the affinity of the receptor molecule toward the pharmaceutical agent, acting as a better and more efficient coenzyme or as an activator by disrupting barriers and removing obstacles for better binding of the agent toward its receptor molecule; for example, enzyme activation by removal of natural inhibitors. In all these cases the overall clinical results would be due to magnified therapeutic effects which are not predictable from either effect alone.

From the point of negative effect, an oligosaccharide aldonic acid or related compound might interfere with or decrease the binding affinity of the pharmaceutical agent toward its receptor molecule; i.e., acting as an competitor or inhibitor. In such case, the overall clinical results should be due to substantial diminishment or completely loss of therapeutic effects, which is also unpredictable from either effect alone.

At present we do not know the exact mechanism involved in the synergistic effect or unexpected increase in therapeutic effect of a cosmetic or dermatological agent by an oligosaccharide aldonic acid. The following are relevant observations.

(1) Not Due to Enhanced Penetration

The enhanced and substantial increase in therapeutic effects of a cosmetic or dermatological agent incorporated with an oligosaccharide aldonic acid is not simply due to an increased penetration of the topical agent into the skin, nor due to a simple addition or combination effects.

(2) Re-activation from Therapeutic Non-responsiveness

Tachyphylaxis or so-called "drug resistance" is frequently encountered with corticosteroid or other drug therapy for topical treatment of psoriasis, eczema etc. On continued topical use, many patients develop tachyphylaxis to corticosteroids, and the lesions very often do not respond any more to topically applied corticosteroid compositions, even under occlusive dressings to enhance penetration. The exact nature of such resistance to the drug is not known. One of the proposed hypotheses is that the available level of receptor molecule(s) for corticosteroids in the skin is diminished or exhausted completely due to continued daily use of the drugs. However, it is not known whether the receptor level is really low or the active site of the receptor molecule is covered-up by an inhibitor.

When tachyphylaxis is encountered from corticosteroid alone therapy, incorporation of an oligosaccharide aldonic acid into the corticosteroid composition would eradicate the drug resistance. If desired, the composition containing an oligosaccharide aldonic acid alone may be applied alternatively with the corticosteroid therapy.

(3) Eradication of Rebound Worsening

One well-known side effect associated with continued use of certain drugs, such as corticosteroids, is a rebound worsening of the disease if the treatment is discontinued. The mechanism of worsening is not known. It has been speculated that the antiinflammatory property of corticosteroids is to suppress the immunological expression of the disease. The disease process is not eradicated nor substantially modified, but is only held-up like river water is held-up by a dam. Discontinuation of the therapy is like removing the dam.

To prevent rebound worsening encountered with corticosteroids is to incorporate an oligosaccharide aldonic acid into the composition containing a corticosteroid, or to use the oligosaccharide aldonic acid alternately with the corticosteroid.

(4) Prevention or Eradication of Side-effects

Other well-known side effects associated with continued topical use of a corticosteroid are thinning and atrophy of the skin. To prevent or eliminate such side effects, an oligosaccharide aldonic acid may be incorporated into the composition containing a corticosteroid, or may be used alternately with the corticosteroid.

We have found that, in most cases, therapeutic effects of cosmetic and pharmaceutical agents are amplified when an oligosaccharide aldonic acid or related compound is incorporated into the composition, i.e., consequence (b) above is observed.

The cosmetic and pharmaceutical agents which may be actuated by oligosaccharide aldonic acids and related compounds include those that improve or eradicate age spots, keratoses and wrinkles; local analgesics and anesthetics; antiacne agents; antibacterials; antiyeast agents; antifungal agents; antiviral agents; antidandruff agents; antidermatitis agents; antihistamine agents; antipruritic agents; antiemetics; antimotionsickness agents; antiinflammatory agents; antihyperkeratolytic agents; antiperspirants; antipsoriatic agents; antiseborrheic agents; hair conditioners and hair treatment agents; antiaging and antiwrinkle agents; sunblock and sunscreen agents; skin lightening agents; depigmenting agents; vitamins; corticosteroids; tanning agents; humectants; hormones; retinoids; gum disease or oral care agents; topical cardiovascular agents; corn, callus and wart removing agents; dipilating agents; and other dermatologicals.

Some examples of cosmetic and pharmaceutical agents are aclovate, acyclovir, acetylsalicylic acid, adapalene, albuterol, aluminum acetate, aluminum chloride, aluminum hydroxide, aluminum chlorohydroxide, amantadine, aminacrine, aminobenzoic acid (PABA), aminocaproic acid, aminosalicylic acid, amitriptyline, anthralin, ascorbic acid, ascoryl palimate, atropine, azelaic acid, bacitracin, bemegride, beclomethasone dipropionate, benzophenone, benzoyl peroxide, betamethasone dipropionate, betamethasone valerate, brompheniramine, bupivacaine, butoconazole, calcipotriene, camphor, capsaicin, carbamide peroxide, chitosan, chlorhexidine, chloroxylenol, chlorpheniramine, ciclopirox, clemastine, clindamycin, clioquinol, clobetasol propionate, clotrimazole, coal tar, cromolyn, crotamiton, cycloserine, dehydroepiandrosterone, desoximetasone, dexarnethasone, diphenhydramine, doxypin, doxylamine, dyclonine, econazole, erythromycin, estradiol, ethinyl estradiol, fluocinonide, fluocinolone acetonide, 5-fluorouracil, griseofulvin, guaifenesin, haloprogin, hexylresorcinol, homosalate, hydrocortisone, hydrocortisone 21-acetate, hydrocortisone 17-valerate, hydrocortisone 17-butyrate, hydrogen peroxide, hydroquinone, hydroquinone monoether, hydroxyzine, ibuprofen, ichthanmol, imiquimod, indomethacin, ketoconazole, ketoprofen, kojic acid, lidocaine, meclizine, meclocycline, menthol, mepivacaine, methyl nicotinate, methyl salicylate, metronidazole, miconazole, minocycline, minoxidil, monobenzone, mupirocin, naftifine, naproxen, neomycin, nystatin, octyl methoxycinnamate, octyl salicylate, oxybenzone, oxiconazole, oxymetazoline, padimate O, permethrin, pheniramine, phenol, phenylephrine, phenylpropanolamine, piperonyl butoxide, podophyllin, podofilox, povidone iodine, pramoxine, prilocaine, procaine, promethazine propionate, propranolol, pseudoephedrine, pyrethrin, pyrilamine, resorcinol, retinal, 13-cis retinoic acid, retinoic acid, retinol, retinyl acetate, retinyl palmitate, salicylamide, salicylic acid, selenium sulfide, shale tar, sulconazole, sulfur, sulfadiazine, tazarotene, terbinafine, terconazole, tetracaine, tetracycline, tetrahydrozoline, thymol, tioconazole, tolnaftate, triamcinolone diacetate, triamcinolone acetonide, triamcinolone hexacetonide, triclosan, triprolidine, undecylenic acid, urea, vitamin E acetate, wood tar, and zinc pyrithione, Another example of cosmetic or other agents that may be combined with one or more oligosaccharide aldonic acids and related compounds include hydroxyacids, ketoacids and related compounds. Examples of hydroxy acids include hydroxymonocarboxylic acids, hydroxydicarboxylic acids, 2-hydroxycarboxylic acids, other hydroxycarboxylic acids, 2-ketocarboxylic acids and related compounds. See, for example, U.S. Pat. Nos. 5,422,370, 5,547,988, 5,470,880, and 5,385,938. The hydroxy acids may exist as a free acid, an ester, a lactone, in salt form with an organic base or an inorganic alkali, and as stereoisomers. Representative examples of hydroxy acids and related compounds include glycolic acid, mandelic acid, lactic acid, tropic acid, methyllactic acid, tartaric acid, citric acid, glucuronic acid, ribonic acid, gluconolactone, ribonolactone, gycolyl glycollate, lactyl lactate, trilactic acid and polylactic acid.

Yet another example of cosmetic or other agents that may be combined with one or more oligosaccharide aldonic acids or related compounds include phenyl alpha acyloxyalkanoic acids and derivatives thereof. These compounds may exist in a free acid, or salt form, or as stereoisomers. See, for example, U.S. Pat. Nos. 5,258,391 and 5,643,949. Representative example of such compounds include diphenyl alpha acetoxyacetic acid, phenyl alpha acetoxyacetic acid, phenyl alpha methyl alpha acetoxyacetic acid, phenyl alpha acetoxypropanoic acid, and 2-phenyl beta acetoxypropanoic acid.

Still another example of cosmetic or other agents that may be combined with one or more oligosaccharide aldonic acids or related compounds include N-acetyl-aldosamines, N-acetylamino acids and related N-acetyl compounds. These compounds may exist in a free acid, lactone or salt form, or as stereoisomers. See, for example, U.S. patent application Ser. No. 09/227,213, filed Jan. 8, 1999. Representative example of such compounds include N-acetyl-glucosamine and N-acetyl-proline.

When the compositions according to the present invention are used for general care, moisturizing, dry skin, skin smoothing and itchy skin, as well as for treatment and prevention, of various cosmetic conditions and dermatological disorders, including those associated with intrinsic and/or extrinsic aging, as well as with changes or damage caused by extrinsic factors, examples of suitable cosmetic or other agents that may be combined with one or more oligosaccharide aldonic acids or related compounds include: hydroxyacids, ketoacids and related compounds; phienyl alpha acyloxyalkanoic acids and derivatives thereof N-acetyl-aldosamines, N-acetylamino acids and related N-acetyl compounds; those that improve or eradicate age spots, keratoses and wrinkles; local analgesics and anesthetics; antiacne agents; antibacterials; antiyeast agents; antifungal agents; antiviral agents; antidandruff agents; antidermatitis agents; antihistamine agents; antipruritic agents; antiemetics; antimotionsickness agents; antiinflammatory agents; antihyperkeratolytic agents; antiperspirants; antipsoriatic agents; antiseborrheic agents; astringents; cleansing agents; hair conditioners and hair treatment agents; antiaging and antiwrinkle agents; sunblock and sunscreen agents; skin lightening agents; depigmenting agents; vitamins; corticosteroids; tanning agents; hormones; retinoids; topical cardiovascular agents; corn, callus and wart removing agents; and other dermatologicals.

Some examples of cosmetic and pharmaceutical agents are aclovate, acyclovir, acetylsalicylic acid, adapalene, albuterol, aluminum acetate, aluminum chloride, aluminum hydroxide, aluminum chlorohydroxide, amantadine, aminacrine, aminobenzoic acid (PABA), aminocaproic acid, arninosalicylic acid, amitriptyline, anthralin, ascorbic acid, ascoryl palimate, atropine, azelaic acid, bacitracin, bemegride, beclomethasone dipropionate, benzophenone, benzoyl peroxide, betamethasone dipropionate, betamethasone valerate, brompheniramine, bupivacaine, butoconazole, calcipotriene, camphor, capsaicin, carbamide peroxide, chitosan, chlorhexidine, chloroxylenol, chlorpheniramine, ciclopirox, clemastine, clindamycin, clioquinol, clobetasol propionate, clotrimazole, coal tar, cromolyn, crotamiton, cycloserine, dehydroepiandrosterone, desoximetasone, dexamethasone, diphenhydramine, doxypin, doxylamine, dyclonine, econazole, erythromycin, estradiol, ethinyl estradiol, fluocinonide, fluocinolone acetonide, 5-fluorouracil, griseofulvin, guaifenesin, haloprogin, hexylresorcinol, homosalate, hydrocortisone, hydrocortisone 21-acetate, hydrocortisone 17-valerate, hydrocortisone 17-butyrate, hydrogen peroxide, hydroquinone, hydroquinone monoether, hydroxyzine, ibuprofen, ichtharnmol, imiquimod, indomethacin, ketoconazole, ketoprofen, kojic acid, lidocaine, meclizine, meclocycline, menthol, mepivacaine, methyl nicotinate, methyl salicylate, metronidazole, miconazole, ninocycline, minoxidil, monobenzone, mupirocin, naftifine, naproxen, neomycin, nystatin, octyl methoxycinnamate, octyl salicylate, oxybenzone, oxiconazole, oxymetazoline, padimate O, permethrin, pheniramine, phenol, phenylephrine, phenylpropanolamine, piperonyl butoxide, podophyllin, podofilox, povidone iodine, pramoxine, prilocaine, procaine, promethazine propionate, propranolol, pseudoephedrine, pyrethrin, pyrilamine, resorcinol, retinal, 13-cis retinoic acid, retinoic acid, retinol, retinyl acetate, retinyl palmitate, salicylamide, salicylic acid, selenium sulfide, shale tar, sulconazole, sulfur, sulfadiazine, tazarotene, terbinafine, terconazole, tetracaine, tetracycline, tetrahydrozoline, thymol, tioconazole, tolnaftate, triamcinolone diacetate, triamcinolone acetonide, triamcinolone hexacetonide, triclosan, triprolidine, undecylenic acid, urea, vitamin E acetate, wood tar, and zinc pyrithione. Other examples of suitable cosmetic and pharmaceutical agents are well known to those of skill in the art.

When the compositions according to the present invention are used for general care, as well as treatment and prevention of diseases and conditions, of the oral and vaginal mucosa, examples of suitable cosmetic or other agents that may be combined with one or more oligosaccharide aldonic acids or related compounds include: hydroxyacids, ketoacids and related compounds; phenyl alpha acyloxyalkanoic acids and derivatives thereof N-acetyl-aldosamines, N-acetylamino acids and related N-acetyl compounds; local analgesics and anesthetics; antibacterials; antiyeast agents; antifungal agents; antiviral agents; antihistamine agents; antipruritic agents; antiemetics; antimotion sickness agents; antiinflammatory agents; vitamins; corticosteroids; hormones; and gum disease or oral care agents.

Some examples of cosmetic and pharmaceutical agents are clotrimazole, ketoconazole, miconazole, griseofulvin, econazole, metronidazole, hydroxyzine, diphenhydramine, pramoxine, lidocaine, procaine, mepivacaine, monobenzone, anthralin, coal tar, benzocaine, benzoyl peroxide, erythromycin, tetracycline, clindamycin, meclocycline, hydroquinone, hydroquinone monoether, minocycine, naproxen, ibuprofen, theophylline, cromolyn, albuterol, retinol, retinyl acetate, retinyl palmitate, retinal, retinoic acid, 13-cis retinoic acid, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol, propionate, benzoyl peroxide, kojic acid, crotamiton, propranolol, promethazine, salicylic acid, vitamin E and vitamin E acetate. Other examples of suitable cosmetic and pharmaceutical agents are well known to those of skill in the art.

When the compositions according to the present invention are used for general oral care, as well as treatment and prevention of oral and gum diseases, examples of suitable cosmetic or other agents that may be combined with one or more oligosaccharide aldonic acids or related compounds include: hydroxyacids, ketoacids and related compounds; phenyl alpha acyloxyalkanoic acids and derivatives thereof N-acetyl-aldosamines, N-acetylamino acids and related N-acetyl compounds; analgesics and anesthetics; antibacterials; antiyeast agents; antifungal agents; antiviral agents; antiinflammatory agents; vitamins; and other gum disease or oral care agents.

Some examples of cosmetic and pharmaceutical agents are triclosan, sodium flouride, zinc chloride, zinc citrate, zinc sulfate, chlorhexidine, chlorhexidine and digluconate.

When the compositions according to the present invention are used for treating skin wounds, for example in aiding the healing of skin cuts, tears, lacerations, burns, punctures, and other wounds, examples of suitable cosmetic or other agents that may be combined with one or more oligosaccharide aldonic acids or related compounds include: hydroxyacids, ketoacids and related compounds; phenyl alpha acyloxyalkanoic acids and derivatives thereof N-acetyl-aldosaniines, N-acetylamino acids and related N-acetyl compounds; analgesics and anesthetics; wound cleansers; antibacterials; antiyeast agents; antifungal agents; antiviral agents; antiinflammatory agents; skin lightening agents; depigmenting agents; vitamins; burn relief agents; and corticosteroids.

(iii) Molecular Complex and Slow-release Compositions

A formulation containing an oligosaccharide aldonic acid usually has a pH of below 3.0, and the composition may irritate human skin of atopic or sensitive skin type on repeated topical application, due to lower pH or uncontrolled release and penetration of the acid into stratum corneum of the skin. We have found that an oligosaccharide aldonic acid can form a buffer system with an alkali and/or a molecular complex with a complexing agent, and the resulting composition has the following attributes: (1) easy and simple process in formulating, (2) raising the overall pH of the formulation to above 3.0, (3) having a buffer system in the composition, (4) no irritation or minimal stinging to sensitive skin, (5) controlled or slow-release of the active ingredient into the skin, and (6) retaining the therapeutic efficacy. The substance used for neutralizing, partially neutralizing, salt forming, buffering or complexing may be an inorganic or organic alkali, or amphoteric.

An alkali is defined as a substance which shows a pH of above 7.0 in a solution. Common inorganic alkalis include for example ammonium hydroxide, ammonium phosphate, ammonium carbonate or bicarbonate, sodium hydroxide, sodium carbonate, sodium bicarbonate, sodium acetate, sodium phosphate, and the like alkalis formed from potassium, calcium, magnesium, strontium, aluminum, zinc, and lithium. Common organic alkalis are amines, hydroxylamines, imines, guanidines, amine oxides, alkanolamines, alkoxylated amines and alkylamido alkylamines, such as diethanolamine, triethanolamine, isopropanolamine, diisopropanolamine, triisopropanolamine, aminobutanol, aminoethyl propanediol, aminomethyl propanol, aminomethyl propanediol, isopropylamine, methylethanolamine, diisopropylamine, dipropylenetriamine, glucamine, N-methylglucamine, morpholine, tromethamine, cocamines, soyamines, oleamines, stearamines, quaterniums and the like. The buffer system in the composition consists of two species; namely oligosaccharide aldonic free acid and oligosaccharide aldonate anion despite an inorganic or organic alkali.

A molecular complexing agent with an oligosaccharide aldonic acid may be an amphoteric or non-amphoteric substance. The mole ratio of a complexing agent may be higher than one, however the preferred ratio is less than one, and most preferred ratio is from 0.1 to 0.5. The amphoteric substance by definition should have both an acidic and a basic functional groups in the molecule, and can behave both as an acid and an alkali in a solution. Inorganic amphoteric substances include certain metallic oxides such as aluminum oxide and zinc oxide. However, the preferred amphoteric system consists of an organic amphoteric substance. The molecule of an organic amphoteric substance should consist of at least one acidic function selected from carboxylic, phosphoric and sulfonic groups, and at least one basic function from amino, imino and guanido groups. Examples of organic amphoteric substances include amino acids, peptides, polypeptides, proteins and related compounds such as glycine, arginine, lysine, cysteine, proline, glutamine, tryptophan, asparagine, tyrosine, ornithine, citrulline, creatine, histidine and canavanine.

In an amphoteric system, the molecular complex consists of several ionic species. For example, a triple ionic complex will be formed from one mole of an oligosaccharide aldonic acid (having one reactive group) with one mole of glycine (having two functional groups), and a quadruple ionic complex will be formed with arginine or lysine (having three functional groups). Due to ionic bonds and forces between the positive charge and the negative charge of the molecular complex ions, the release and penetration of the oligosaccharide aldonic acid into the skin will be controlled at moderate and optimal rate. Thus the slow-release system can reduce or eliminate skin irritation without compromising the intended therapeutic effects.

The non-amphoteric complexing agents are organic alkalis which include organic amines, polyamines, hydroxylamines, imines, guanidines, amine oxides, alkanolamines, alkoxylated amines, alkylamido alkylamines, amino acid esters, amino acid amides, aminosaccharides, aminoalditols, aminocyclitols, fattyamines, imidazolines and the like which are capable of forming the molecular complex and/or salts with oligosaccharide aldonic acids. The molecular weight of a complexing agent may range from 50 to 10,000, however the preferred one ranges from 100 to 600. Examples of some complexing agents include creatinine, glycine ethyl ester, arginine ethyl ester, lysine methyl ester, proline ethyl ester, citrulline benzyl ester, glycinamide, argininamide, prolinamide, lysinamide, glucamine, methylglucamine, glucosamines and glucosylamines, other glycosamines and glycosylamines, aminoinositols, chitosan, stearamidoethyl diethylamine, stearamidopropyl dimethylamine, stearamidoethyl diethanolamine, quaternary ammonium hydroxide.

(iv) Antioxidant Properties

An antioxidant may be defined as a substance capable of preventing or inhibiting oxidation. Most oligosaccharide aldonic acids are antioxidant compounds because they possess two or more hydroxyl groups near the carboxylic group. The antioxidant property is readily determined by using any one of the following test methods: prevention or retardation of air oxidation of (a) anthralin, (b) hydroquinone, or (c) banana peel. A freshly prepared anthralin solution or cream is bright yellow, and an air oxidized one is brownish or black. A hydroquinone solution or cream is colorless or white color, and an air oxidized one is brownish or black. A freshly peeled banana peel is light yellow in color and an oxidized one ranges in color from tan, dark tan, brown to brownish black.

For example, in control experiments, fresh banana peels cut into sizes of 1×2 cm in 50 mm plastic petri dishes containing 5 ml water at neutral or acidic pH changed in color from white-yellowish to tan within 6 hours at room temperature, and changed to dark tan color during the next period of 24 to 72 hours. When fresh banana peels were placed in dishes containing 5 ml of 0.1 M lactobionic acid under the same conditions, the banana peels remained white-yellowish for the period of 24 hours, and changed in color to tan after 72 hours. The above test results show that lactobionic acid is an antioxidant substance. Using anthralin and hydroquinone test methods also confirmed that lactobionic acid is a moderate antioxidant.

(v) Gel Matrix Formation

In contrast to an alpha hydroxyacid and polyhydroxyacid, an oligosaccharide aldonic acid can form a gel matrix when its aqueous solution is evaporated at room temperature. The transparent gel obtained retains certain amount of water forming a clear gel matrix. The amount of water retention depends on individual oligosaccharide aldonic acid. Examples of gel matrix preparations are provided below.

The formation of a gel matrix between an oligosaccharide aldonic acid and water has been found to have moisturizing, soothing, healing and slow-release effects in addition to other various beneficial effects to skin, mucous membrane, hair and nail. The beneficial effects from an oligosaccharaide aldonic acid within the skin, nail and hair are expected to include those provided by glycosaminoglycans (GAGs). This is due to similarities in the basic chemical structure of oligosaccharaide aldonic acids and GAGs, and the fact that they both form a gel matrix with water. Exemplary beneficial effects and functions of GAGs inside the skin includes (i) binding with polycations and cations, such as sodium and potassium ions, to enhance water retention, and (ii) specific interaction with collagen, elastin, fibronectin, laminin and other proteins to stabilize the turgor of the skin.

3. General Preparation of the Cosmetic and Therapeutic Compositions (i) General Preparation Compositions comprising an oligosaccharide aldonic acid or related compound of the instant invention may be formulated as solution, gel, lotion, cream, ointment, shampoo, spray, stick, powder, masque, mouth rinse or wash, vaginal gel or preparation, or other form acceptable for use on skin, nail, hair, oral mucosa, vaginal mucosa, mouth or gums.

To prepare a solution composition, at least one oligosaccharide aldonic acid or related compound of the instant invention is dissolved in a solution prepared from water, ethanol, propylene glycol, butylene glycol, and/or other topically acceptable vehicle. The concentration of a single oligosaccharide aldonic acids or related compound or the total concentration of all oligosaccharide aldonic acids and related compounds, where the composition comprises more than one oligosaccharide aldonic acids or related compounds, may range from 0.01 to 99.9% by weight of the total composition, with preferred concentration of from 0.1 to 50% by weight of the total composition and with more preferred concentration of from 0.5 to 25% by weight of the total composition. Contemplated embodiments of the instant invention include ranges of 0.1% to 0.2%, 0.2% to 0.3%, 0.3% to 0.4%, 0.4% to 0.5%, 0.5% to 0.6%, 0.6% to 0.7%, 0.7% to 0.8%, 0.8% to 0.9%, 0.9% to 1%, 1% to 2%, 2% to 3%, 3% to 4%, 4% to 5%, 5% to 6%, 6% to 7%, 7% to 8%, 8% to 9%, 9% to 10%, 10% to 14%, 14% to 18%, 18% to 22%, 22% to 26%, 26% to 30%, 30% to 35%, 35% to 40%, 40% to 45%, 45% to 50%, 50% to 60%, 60% to 70%, 70% to 80%, 80% n to 90%, and 90% to 99.9% by weight of the total composition.

To prepare a topical composition in lotion, cream or ointment form, the oligosaccharide aldonic acid or related compounds is first dissolved in water, ethanol, propylene glycol, and/or another vehicle, and the solution thus obtained is mixed with a desired base or pharmaceutically acceptable vehicle to make lotion, cream or ointment. Concentrations of the oligosaccharide aldonic acid or related compounds are the same as described above.

A topical composition of the instant invention may also be formulated in a gel or shampoo form. A typical gel composition is formulated by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate to a solution comprising the oligosaccharide aldonic acid or related compound. The preferred concentration of the gelling agent may range from 0.1 to 4 percent by weight of the total composition. In the preparation of shampoo, the oligosaccharide aldonic acids or related compounds is first dissolved in water or propylene glycol, and the solution thus obtained is mixed with a shampoo base. Concentrations of the oligosaccharide aldonic acids or related compounds used in gel or shampoo form are the same as described above.

To prepare a combination composition for synergetic effects, a cosmetic, pharmaceutical or other topical agent is incorporated into any one of the above compositions by dissolving or mixing the agent into the formulation.

Other forms of compositions for delivery of oligosaccharide aldonic acids and related compounds of the instant invention are readily blended, prepared or formulated by those skilled in the art.

(ii) Gel Matrix Preparations

In contrast to an alpha hydroxyacid and polyhydroxyacid, an oligosaccharide aldonic acid can form a gel matrix. A gel matrix may be formed on the skin, hair, nail or mucosa when a solution comprising an oligosaccharide aldonic acid undergoes evaporation.

In one example, a gel matrix can be formed when aqueous solution comprising an oligosaccharide aldonic acid is evaporated at room temperature. The transparent gel thus obtained retains certain amount of water forming a clear gel matrix. The amount of water retention depends on individual oligosaccharide aldonic acid. For example, maltobionic acid 1 g in a beaker was dissolved in water 1 ml, and the solution thus obtained was left at room temperature. Fifty percent of the original water had been evaporated at the end of 24 hours, and 57% at the end of 48 hours, and 60% at the end of 72 hours, and no more or minimal evaporation of water could be detected after 72 hours. A clear gel film thus obtained contained 29% water complexed with maltobionic acid molecules. In the same manner, lactobionic acid formed a clear gel matrix with 14% water molecules and cellobionic acid formed a transparent gel with 7% water molecules. The formation of a gel matrix between an oligosaccharide aldonic acid and water has been found to have soothing, healing and slow-release effects in addition to other various beneficial effects to skin, mucous membrane, hair and nail.

The following are illustrative examples of formulations and other aspects of the present invention. Although the examples utilize only selected compounds and formulations, it should be understood that the following examples are illustrative and not limiting. Therefore, any of the aforementioned oligosaccharide aldonic acids or related compounds may be substituted according to the teachings of this invention in the following examples.

EXAMPLE 1

A typical experiment to determine a gel matrix formation of an oligosaccharide aldonic acid may be carried out as follows.

Maltobionic acid 1 g in a beaker of 3.6 cm diameter and 3.6 cm height was dissolved in water 1 ml, and the solution thus obtained was left at room temperature between 20–25° C. to allow a slow evaporation of the water. Fifty percent of original water had been evaporated at the end of 24 hours, 57% at the end of 48 hours, 60% at the end of 72 hour and 60.5% at the end of 96 Hours. A clear continuous gel film was formed at the end of 72 hours, and this was confirmed by observation under a microscope and determination from its physical characteristics. The continuous transparent film thus obtained consisted of 71% maltobionic acid and 29% water by weight, and was formed as a complex gel matrix between maltobionic acid molecules and water molecules.

Under the same conditions, a clear continuous gel film was formed from lactobionic acid 1 g and water 1 ml. The continuous film thus obtained consisted of 86% lactobionic acid and 14% water by weight, and was formed as a complex gel matrix between lactobionic acid molecules and water molecules.

Under the same experiment, a clear continuous gel film was formed from cellobionic acid 1 g and water 1 ml. The continuous film thus obtained consisted of 93% cellobionic acid and 7% water by weight, and was formed as a complex gel matrix between cellobionic acid molecules and water molecules.

Under the same conditions and experiment, gluconic acid did not form any form of a gel matrix.

EXAMPLE 2

Antioxidant property of an oligosaccharide aldonic acid may be determined by utilizing anthralin test method as follows.

Anthralin also known as dithranol is a yellowish powder, and a composition containing anthralin without a suitable antioxidant is chemically unstable even at room temperature. For example, anthralin 0.05% in an oil-in-water cream changed in color from yellow to gray within 24 hours at room temperature, and the cream became brownish within 48 hours. Under anhydrous condition, anthralin 0.05% ointment prepared from white petrolatum 2 parts and mineral oil 1 part by weight changed in color from bright yellow to grayish yellow within 24 hours, and the ointment became brownish after 12 days at room temperature.

Based on the above observations, an oil-in-water cream containing 0.4% anthralin with or without a known antioxidant was used as a positive or vehicle control. The final concentration of a test substance or antioxidant was 0.1 M. It was found that while the control cream without an antioxidant changed in color from yellow to grey within 24 hours, the positive control cream with a known antioxidant (vitanmin C or oxalic acid) and the test cream containing lactobionic acid, maltobionic acid or cellobionic acid did not change the color within 24 hours. These results indicated that the bionic acids are comparably equal to vitamin C and oxalic acid as antioxidant substances.

EXAMPLE 3

Antioxidant property of an oligosaccharide aldonic acid may also be determined by utilizing hydroquinone test method as follows. Hydroquinone also known as 1,4-dihydroxybenzene is a white powder, and a composition containing hydroquinone without a suitable antioxidant is chemically unstable even at room temperature. For example, hydroquinone 2% in an oil-in-water cream changed in color from white to grey within 2 hours, and the cream became light brown within 48 hours and dark brown after 72 hours at room temperature. Under the same test conditions, the cream containing 2% hydroquinone and 0.4 M concentration of a known antioxidant (vitamin C, citric acid or N-acetylcysteine), maltobionic acid, lactobionic acid or cellobionic did not change color even after 5 days. These results indicated that the bionic acids are comparably equal to vitamin C, citric acid and N-acetylcysteine as antioxidant substances.

EXAMPLE 4

Antioxidant property of an oligosaccharide aldonic acid may also be determined by utilizing banana peel test method as follows.

A fresh ripe banana peel cut into sizes of 2×2 cm has the outer layer light yellow in color. These freshly cut banana peels after exposed to air or immersed in an aqueous solution without an antioxidant in 50 mm plastic petri dishes rapidly changed in color from yellowish to tan within 3 hours, dark tan within 24 hours and brown black after 72 hours. A test substance including a positive control such as vitamin C, citric acid or N-acetylcysteine was prepared as 0.1 M concentration, and each test dish contained 5 ml test solution. Freshly cut banana peels 2×2 cm in sizes were immersed in 5 ml test solutions including known antioxidants and vehicle controls with pH at 7.0 and 4.0. It was found that while the banana peels immersed in water alone changed in color from white yellowish to tan within 4 hours, the banana peels did not change color in the solution containing maltobionic acid or lactobionic acid. The same results were also found for the known antioxidant substances; vitamin C, citric acid and N-acetylcysteine. These results indicated that the bionic acids are antioxidant substances.

EXAMPLE 5

Typical solution compositions suitable for topical use on hair, scalp, nail or skin, or use for wound healing, or for general care of oral or vaginal mucosa comprising an oligosaccharide aldonic acid may be formulated as follows.

(a) Maltobionic acid 50% aqueous solution was prepared by dissolving maltobionic acid 50 g in 50 ml water. This solution 10 g was mixed with a vehicle 90 ml prepared from ethanol 40 parts, water 40 parts and propylene glycol 20 parts by volume. The composition had pH 3.1 and contained 5% maltobionic acid.

(b) Cellobionic acid 25% aqueous solution was prepared by dissolving cellobionic acid 25 g in 75 ml water. This solution 40 g was mixed with a vehicle 60 ml prepared from ethanol 40 parts, water 40 parts and propylene glycol 20 parts by volume. The composition had pH 3.5 and contained 10% cellobionic acid.

(c) Lactobionic acid 0.5 g was dissolved in 99.5 ml solution prepared from water 40 parts, ethanol 40 parts and propylene glycol 20 parts by volume. The composition had pH 2.6 and contained 0.5% lactobionic acid.

A solution composition with pH 1.9 containing 10% lactobionic acid was formulated from 10 g lactobionic acid dissolved in water 50 ml, ethanol 20 ml and propylene glycol 20 ml.

A solution composition with pH 2.1 containing 25% lactobionic acid was formulated from lactobionic acid 50% aqueous solution 50 g and enough ethanol to make a total volume of 100 ml.

EXAMPLE 6

Typical shampoo compositions comprising an oligosaccharide aldonic acid for hair, scalp or body wash may be formulated as follows.

Maltobionic acid 50% aqueous solution 10 g was mixed uniformly with a shampoo base 90 g. The composition had pH 2.9 and contained 5% maltobionic acid.

Cellobionic acid 25% aqueous solution 20 g was mixed uniformly with a shampoo base 80 g. The composition had pH 3.9 and contained 5% cellobionic acid.

Lactobionic acid 10 g was dissolved in 20 ml water, and the solution thus obtained was mixed uniformly with a shampoo base 70 g. The composition had pH 2.6 and contained 10% lactobionic acid.

EXAMPLE 7

Typical cream compositions comprising an oligosaccharide aldonic acid for cosmetic or dermatological indications, or for general care of nail, skin or mucous membranes may be formulated as follows.

Maltobionic acid 50% aqueous solution 50 g was mixed with an oil-in-water base 50 g. The composition had pH 1.7 and contained 25% maltobionic acid.

Cellobionic acid 25% aqueous solution 20 g was mixed with an oil-in-water base 80 g. The composition had pH 3.3 and contained 5% cellobionic acid.

Lactobioic acid 2 g was dissolved in 18 ml water, and the solution thus obtained was mixed uniformly with a cream base 80 g or commercially available hydrophilic ointment. The white cream thus formulated had pH 2.2 and contained 2% lactobionic acid.

A cream composition with pH 1.7 contained 10% lactobionic acid was formulated from lactobionic acid 10 g, water 10 ml and cream base 80 g.

A cream composition with pH 1.8 contained 18% lactobionic acid was formulated from lactobionic acid 54% aqueous solution 33.3 g and a cream base 66.7 g.

A cream composition with pH 1.7 contained 27% lactobionic acid was formulated from lactobionic acid 54% aqueous solution 50 g and a cream base 50 g.

EXAMPLE 8

Typical gel compositions comprising an oligosaccharide aldonic acid for cosmetic or dermatological indications, wound healing, or for general care of hair, scalp, nail, skin, oral or vaginal mucosa may be formulated as follows.

Maltobionic acid 50% aqueous solution 20 g was mixed uniformly with a gel base 80 g. The composition had pH 2.9 and contained 10% maltobionic acid.

Cellobionic acid 6 g was dissolved in water 18 ml, and the solution thus obtained was mixed with a gel base 76 g. The composition had pH 3.9 and contained 6% cellobionic acid.

Lactobionic acid 54% aqueous solution 9.3 g was mixed uniformly with a gel base 90.7 g. The gel composition thus formulated had pH 3.0 and contained 5% lactobionic acid.

EXAMPLE 9

Typical water-in-oil compositions comprising an oligosaccharide aldonic acid for cosmetic or dermatological indications, wound healing, or for general care of nail, skin, oral or vaginal mucosa may be formulated as follows.

Maltobionic acid 50% aqueous solution 20 g was mixed uniformly with a water-in-oil base 80 g. The water non-washable composition thus formulated contained 10% maltobionic acid.

Cellobionic acid 25% aqueous solution 20 g was mixed uniformly with a water-in-oil base 80 g. The water non-washable composition thus formulated contained 5% cellobionic acid.

EXAMPLE 10

Typical masque compositions comprising an oligosaccharide aldonic acid for cosmetic or dermatological indications of nail, or skin for example on the face, may be formulated as follows.

Maltobionic acid 50% aqueous solution 16 g was mixed uniformly with a masque base 84 g. The masque composition thus formulated contained 8% maltobionic acid.

Cellobionic acid 25% aqueous solution 36 g was mixed uniformly with a masque base 64 g. The masque composition thus formulated contained 8% cellobionic acid.

EXAMPLE 11

A typical synergetic composition comprising an oligosaccharide aldonic acid in combination with an anti-fungal agent for infections of nail, scalp, hair, skin, oral or vaginal mucosa may be formulated as follows.

Lactobionic acid 10 g was dissolved in 90 ml solution prepared from water 40 ml, ethanol 40 ml and propylene glycol 20 ml. The composition thus formulated contained 10% lactobionic acid, and was used as a nail or scalp conditioner.

For fungal infections, lactobionic acid 10 g and clotrimazole 2 g were dissolved in 88 ml solution prepared from water 60 ml, ethanol 20 ml and propylene glycol 20 ml. The synergetic composition thus formulated had pH 3.3 and contained 10% lactobionic acid and 2% clotrimazole, and were suitable for treatment of fungal infections of nail, scalp, hair, skin, oral or vaginal mucosa.

EXAMPLE 12

A typical synergetic composition comprising an oligosaccharide aldonic acid in combination with a corticosteroid for eczema, psoriasis or other inflammatory dermatoses may be formulated as follows.

Lactobionic acid 5 g was dissolved in 10 ml water, and hydrocortisone 17-valerate 0.2 g was dissolved in 10 ml warm propylene glycol. Two solutions thus prepared were added to and mixed uniformly with 74.8 g cream base or commercially available hydrophilic ointment. The white cream thus formulated contained 5% lactobionic acid and 0.2% hydrocortisone 17-valerate.

EXAMPLE 13

A typical synergetic composition comprising an oligosaccharide aldonic acid in combination with an anti-acne agent may be formulated as follows.

Lactobionic acid 54% aqueous solution 11 g and salicylic acid 2 g were dissolved and mixed with 87 ml solution prepared from ethanol 70 ml and propylene glycol 30 ml. The synergetic composition thus formulated had pH 3.1, and contained 6% lactobionic acid and 2% salicylic acid.

EXAMPLE 14

In one of the studies related to skin changes associated with aging, skin thickness was measured by micrometer calipers as follows:

The skin was grasped with a 2×6 cm metal hinge; the internal faces of which were coated with emery cloth to prevent slippage, and manually squeezed to threshold subject discomfort. Combined thickness of two whole-skin layers including thickness of the two hinge leaves was measured with micrometer calipers. Thickness of the two hinge leaves was subtracted to determine the actual thickness of two whole-skin layers. Triplicate measurements on treated sites were done and an average number was used for calculation of the skin thickness.

EXAMPLE 15

A female subject, age 56, topically applied twice daily to her left forearm for four weeks lactobionic acid 22% in a solution prepared from water 7 parts and propylene glycol 3 parts. After four weeks her right forearm was still loose and relatively thin, and the skin was relatively rough and dry. In contrast, her left forearm was more firm and plump, and the skin was smooth, soft and not dry. While there was no change in skin thickness of her right forearm, her left forearm had increased 12% in skin thickness as measured by the micrometer calipers described in the Example. These results indicated that lactobionic acid would be topically effective and beneficial for various cosmetic and dermatological indications.

EXAMPLE 16

A male subject, age 66, with chronic atopic eczema and pruritic dry skin topically applied twice daily maltobionic acid 17% cream to itchy skin areas of eczema and dry skin lesions for two weeks. The treated skin became smooth and less dry and itchy within a week of topical application. The eczema lesions improved significantly after two weeks of topical treatment with maltobionic acid.

EXAMPLE 17

A female subject, age 59, having xerosis with flaky dry skin condition of her forearms topically applied twice daily maltobionic acid 5% water-in-oil cream for two weeks. After two weeks, her forearms became smooth and soft, and the dry skin condition disappeared completely.

EXAMPLE 18

A male subject, age 60, having two skin fissures (open cuts) 2–3 mm long at the finger tips, extending from the hyponychia, topically applied twice daily lactobionic acid 10% oil-in-water cream to one fissure for one week. The other fissure was treated with a vehicle control. While the control site remained unhealed and painful, the skin treated with the active cream healed rapidly, and the pain disappeared after a few days of topical application. After a week of topical treatment with the active cream, the skin fissure healed completely while the control site remained unhealed. This result indicated that the oligosacchardie aldonic acid would be topically effective for promoting wound healing of the skin.

EXAMPLE 19

A typical composition comprising molecular complex of an oligosaccharide aldonic acid in amphoteric system may be formulated as follows. Lactobionic acid 7.2 g (0.02 mole) was dissolved in 14.4 ml water, and the solution containing 33.3% active ingredient had pH 1.9. L-Arginine 0.88 g (0.005 mole) was added to the solution with stirring to form molecular complex as shown by an increase in pH of the solution. The complexing reaction was completed as indicated by no more increase in pH of the solution. The final pH of the solution was 3.4, and the solution was mixed with sufficient quantity of water-in-oil cream to make a total composition of 100 g by weight. The water-non-washable cream thus formulated contained molecular complex of 7.2% lactobionic acid and 0.88% L-arginine.

EXAMPLE 20

A typical synergetic composition comprising molecular complex of an oligosaccharide aldonic acid in combination with skin lightening agents may be formulated as follows.

Maltobionic acid 50% aqueous solution 14.4 g was diluted with 7.2 ml water, and the solution had pH 1.6. L-Lysine 1.16 g was added to form molecular complex as shown by the increase of pH to 3.3. In another container, hydroquinone 2 g and kojic acid 1 g were dissolved in warm propylene glycol 12 g, and this solution together with the above molecular complex solution were mixed with oil-in-water cream to make a total composition of 100 g by weight. The synergetic cream thus formulated contained 2% hydroquinone and 1% kojic acid in molecular complex of 7.2% maltobionic acid and 1.2% L-lysine.

EXAMPLE 21

A typical synergetic composition comprising vitamin A and vitamin E may be formulated as follows.

Cellobionic acid 3 g was dissolved in water 16 ml and propylene glycol 4 ml, and L-arginine 0.4 g was added to the solution with stirring to form an amphoteric complex. This complex and retinyl acetate 2 g and tocopheryl acetate 2 g were mixed with an oil-in-water cream to make a total composition of 100 g by weight. The amphoteric composition thus formulated had pH 5,5, and contained 3% cellobionic acid, 2% vitamin A and 2% vitamin E. This composition is topical effective for various cosmetic and dermatological indications.

EXAMPLE 22

Lactobionic acid 50% aqueous solution 10 g was diluted with 60 ml water and 10 ml propylene glycol, and the solution had pH 2.1. L-Arginine 5% solution 20 g prepared from 8 parts water and 2 parts propylene glycol by volume was added to form molecular complex of amphoteric system as shown by the increase of pH to 3.3. The composition thus formulated contained 5% lactobionic acid in molecular complex with 1% L-arginine.

A male subject, age 67, having chronic gum disease of bleeding during the tooth brushing, used the above bionic acid complex composition twice daily as a gurgling solution with at least one minute of contact time in oral cavity. No food or drink was taken for the next 30 minutes. After one week of such oral treatment with the bionic acid composition, the gum bleeding stopped or became less noticeable during the tooth brushing. This result suggests that the oligosacchardie aldonic acid would be effective or beneficial for treatment of gum diseases.

EXAMPLE 23

Lactobionic acid 50% aqueous solution 10 g was uniformly mixed with an oil-in-water base 80 g, and the cream thus obtained had pH 2.5. L-Arginine 5% solution 10 g prepared from 8 parts water and 2 parts propylene glycol by volume was added to form molecular complex of amphoteric system as shown by the increase of pH to 3.1. The composition thus formulated contained 5% lactobionic acid in molecular complex with 0.5% L-arginine.

A female subject, age 60, having dry vaginal mucosa topically applied the above bionic acid cream twice daily to the affected areas of the mucosa. After one week of topical applications, the dryness of vaginal mucosa disappeared completely and the mucosa became smooth and moist. This result suggests that the oligosaccharide aldonic acid would be therapeutically effective for topical treatment of dry vaginal mucosa.

EXAMPLE 24

Lactobionic acid 54% aqueous solution 30 g was uniformly mixed with an oil-in-water base 60 g. The cream thus prepared had pH 2.0 and contained 18% lactobionic acid.

A male subject, age 66, having a lasting scrotum and perineum itch after each time taking a shower topically applied the above bionic acid cream to the affected areas of the skin. The itch stopped immediately after topical application of the cream. This result suggests that the oligosaccharide aldonic acid would be therapeutically effective and beneficial for topical treatment of senior itch or itch of unknown causes.

EXAMPLE 25

A sterile 22-gauge needle was held in the jaws of a surgical needle holder, and two linear wounds 1 cm in length and 0.5 mm in depth were made on alchohol-swabbed left forearm of a healthy male subject, age 76. The wounds were swabbed dry with cotton balls. A control solution containing 0.9% sodium chloride in distilled water was applied to one wound, and a test solution containing 2% lactobionic acid in distilled water was applied to the other wound. Both wounds were covered with 3M Tegaderm tapes for five days. At the end of one week, whereas the control wound was not epithelialized, the test wound was healed with re-epithelialization. The erythema disappeared from both skin sites at the end of nine days.

These test results showed that a bionic acid was topically effective for improving wound healing.

EXAMPLE 26

A sterile 4 mm skin biopsy punch was used to make two circular wounds 0.5 mm in depth on alcohol-swabbed left forearm of a healthy male subject, age 76. The wounds were swabbed dry with cotton balls. A control solution containing 0.9% sodium chloride in distilled water was applied to one circular wound, and a test solution containing 2% lactobionic acid in distilled water was applied to the other circular wound. Both wounds were covered with 3M Tegaderm tapes for five days. At the end of one week, the control wound was not epithelialized and the test wound was healed with re-epithelialization. The erythema disappeared from both skin sites at the end of nine days.

These test results showed that a bionic acid was topically effective for improving wound healing.

EXAMPLE 27

A female subject, age 60, developed contact dermatitis or erythema on her face after topical applications of 20% unneutralized glycolic acid cream. She applied 5% partially neutralized lactobionic acid cream on the left side of her face and a control cream on the right side of her face. Whereas the erythema persisted on the right side of her face, the skin on the left side of her face improved substantially and the erythema became less noticeable after three topical applications of lactobionic acid cream over the 24 hour period.

These results showed that a bionic acid was topically effective in reducing skin irritations caused by an external factor.

EXAMPLE 28

A male subject, age 67, with sensitve skin developed acute erythema on his both thighs after taking hot shower using alkaline soap. He applied 3% partially neutralized maltobionic acid cream on his left thigh and a control cream on his right thigh. Whereas the erythema and itch persisted on his right thigh, the erythema and itch disappeared within a few minutes after topical application of maltobionic acid cream.

These results showed that a bionic acid was topically effective in reducing skin irritations caused by an external factor.

The invention described herein may be embodied in other specific forms without departing from the spirit or essential characteristics thereof. The specific embodiments previously described are therefore to be considered as illustrative of, and not limiting, the scope of the invention. Additionally, the disclosure of all patents or patent applications, including U.S. provisional application Serial No. 60/141,624, and all publications cited above are expressly incorporated herein by reference in their entireties to the same extent as if each were incorporated by reference individually.

We claim:

1. A composition comprising (A) an acceptable vehicle or base and (B) a therapeutically effective amount of at least one compound selected from the group consisting of isolactobionic acid, maltobionic acid, isomaltobionic acid, cellobionic acid, gentiobionic acid, laminarabionic acid, melibionic acid, nigerobionic acid, rutinobionic acid, sophorobionic acid, and kojibionic acid as isomeric, nonisomeric, free acid, ester, salt, partial salt, lactone, saturated or unsaturated, and straight or branched chain, or cyclic forms thereof.

2. The composition of claim 1, further comprising a cosmetic, pharmaceutical, or other topical agent.

3. The composition of claim 2, wherein said cosmetic, pharmaceutical, or other topical agent is selected from the group consisting of agents that improve or eradicate age spots, keratoses and wrinkles; local analgesics and anesthetics; antiacne agents; antibaclerials; antiyeast agents; antifungal agents; antiviral agents; antidandruff agents; antidermatitis agents; antihistamine agents; antipruritic agents; antiemetics; antimotion sickness agents; antiinflammatory agents; antihyperkeratolytic agents; antiperspirants; antipsoriatic agents; antiseborrheic agents; hair conditioners and hair treatment agents; antiaging and antiwrinlde agents; sunblock and sunscreen agents; skin lightening agents; depigmenting agents; vitamins; corticosteroids; tanning agents; hormones; amino acids; dipeptides; tripeptides; oligopeptides; polypeptides; retinoids; topical cardiovascular agents; hydroxyacids, ketoacids and related compounds; phenyl alpha acyloxyalkanoic acids and derivatives thereof; and N-acetyl-aldosamines, N-acetylamino acids and related N-acetyl compounds.

4. The composition of claim 3, wherein said cosmetic, pharmaceutical, or other topical agent is selected from the group consisting of aclovate, acyclovir, acetylsalicylic acid, adapalene, albuterol, aluminum acetate, aluminum chloride, aluminum hydroxide, aluminum chlorohydroxide, amantadine, aminacrine, aminobenzoic acid (PABA), γ-aminobutanoic acid, aminocaproic acid, aminosalicylic acid, amitriptyline, anserine, anthralin, ascorbic acid, ascorbyl palimate, atropine, azelaic acid, bacitracin, bemegride, beclomethasone dipropionate, benzocaine, benzophenone, benzoyl peroxide, betamethasone dipropionate, betamethasone valerate, brompheniramine, bupivacaine, butoconazole, calcipotriene, camphor, capsaicin, carbamide peroxide, camosine, chitosan, chlorhexidine, chloroxylenol, chlorpheniramine, ciclopirox, clemastine, clindamycin, clioquinol, clobetasol propionate, clotrimazole, coal tar, cromolyn, crotamiton, cycloserine, dehydroepiandrosterone, desoximetasone, dexamethasone, diphenhydramine, doxypin, doxylamine, dyclonine, econazole, erythroinycin, estradiol, ethinyl estradiol, fluocinocide, fluocinolone acetonide, 5-fluorouracil, glutathione, griseofulvin, guaifenesin, haloprogin, hexyiresorcinol, homocarnosine, homosalate, hydrocortisone, hydrocortisone 21-acetate, hydrocortisone 17-valerate, hydrocortisone 17-butyrate, hydrogen peroxide, hydroquinone, hydroquinone monoether, hydroxyzine, ibuprofen, icbthammol, imiquimod, indomethacin, ketoconazole, ketoprofen, kojic acid, lidocaine, meclizine, meclocycline, menthol, mepivacaine, methyl nicotinate, methyl salicylate, metronidazole, miconazole, minocycline, minoxidil, monobenzone, mupirocin, naftifine, naproxen, neomycin, nystatin, octyl methoxycinnamate, octyl salicylate, ophidine, ornithine, oxybenzone, oxiconazole, oxymetazoline, padimate O, permethrin, pheniramine, phenol, phenylephrine, phenyipropanolamine, piperonyl butoxide, podophyllin, podofilox, povidone iodine, polymyxins, pramoxine, prilocaine, procaine, promethazine propionate, propranolol, pseudoephedrine, pyrethrin, pyrilamine, resorcinol, retinal, 13-cis retinoic acid, retinoic acid, retinol, retinyl acetate, retinyl palmiltate, salicylamide, salicylic acid, selenium sulfide, shale tar, sulconazole, sulfur, sulfadiazine, tazarotene, terbinafine, terconazole, tetracaine, tetracycline, tetrahydrozoline, thymol, tioconazole, tolnaftate, triamcinolone diacetate, triamcinolone acetonide, triamcinolone hexacetonide, triclosan, triprolidine, undecylenic acid, urea, vitamin E acetate, wood tar, zinc pyrithione, glycolic acid, lactic acid, methyllactic acid, 4-hydroxy-mandelic acid, mandelic acid, gluconolactone, N-acetyl-glucosamine, N-acetyl-proline, phenyl 2-acetoxyethanoic acid and diphenyl 2-acetoxyethanoic acid.

5. The composition of claim 1, further comprising an inorganic or organic alkali, or amphoteric substance.

6. The composition of claim 5, wherin said inorgainc alkali is selected from the group consisting of ammonium hydroxide, ammonium phosphate, ammonium carbonate, ammonium bicarbonate, sodium hydroxide, sodium carbonate, sodium bicarbonate, sodium acetate, sodium phosphate, and alkalis formed from potassium, calcium, magnesium, strontium, aluminum, zinc, and lithium.

7. The composition of claim 5, wherein said organic alkali is selected from the group consisting of amines, hydroxylamines, imines, guanidines, amine oxides, alkanolamines, alkoxylated amines, alkylamido alkylamines, organic amines, polyamines, hydroxylamines, amino acid esters, amino acid amides, aminosaccharides, aminoalditols, aminocyclitols, fattyamines, and imidazolines.

8. The composition of claim 5, wherein said organic alkali is selected from the group consisting of diethanolamine, triethanolamine, isopropanolamine, diisopropanolamine, triisopropanolamine, aminobutanol, aminoethyl propanediol, aminomethyl propanol, aminomethyl propanediol, isopropylamine, dimethylaminoethanol, diethylaminoethanol, methylethanolamine, diisopropylamine, dipropylenetriamine, glucamine, N-methylglucamine, morpholine, tromethamine, cocamines, soyamines, oleamines, stearamines, quaterniums, creatinine, glycine ethyl ester, arginine ethyl ester, lysine methyl ester, proline ethyl ester, citrulline benzyl ester, glycinamide, argininamide, prolinamide, lysinamide, glucamine, methylgiucamine, glucosarmines and glucosylamines, other glycosamines and glycosylamines, aminoinositols, chitosan, stearamidoethyl diethylamine, stearamidopropyl dimethylamine, stearamidoethyl diethanolamine, and quatemary ammonium hydroxide.

9. The composition of claim 8, wherein said amphoteric substance is selected from the group consisting of amino acids, peptides, polypeptides, proteins and related compounds.

10. The composition of claim 8, wherein said amphoteric substance is selected from the group consisting of glycine, arginine, lysine, cysteine, proline, glutamine, histidine, asparagine, tyrosine, ornithine, citrulline, creatine, creatinine, and tryptophan.

11. A method for treating or preventing cosmetic conditions or dermatological disorders, comprising topically applying a composition comprising (A) a topically acceptable vehicle or base and (B) a therapeutically effective amount of at least one compound selected from the group consisting of isolactobionic acid, maltobionic acid, isomaltobionic acid, cellobionic acid, gentiobionic acid, laminarabionic acid, melibionic acid, nigerobionic acid, rutinobionic acid, sophorobionic acid, and kojibionic acid as isomeric, nonisomeric, free acid, ester, salt, partial salt, lactone, saturated or unsaturated, and straight or branched chain, or cyclic forms thereof.

12. The method of claim 11, wherein said cosmetic conditions or dermatological disorders are selected from the group consisting of disturbed keratinization, defective syntheses of dermal components, and changes associated with aging of skin, nail and hair; and those indications which include dryness or loose of skin, nail and hair; xerosis; ichthyosis; palmar and plantar hyperkeratoses; uneven and rough surface of skin, nail and hair; dandruff; Darier's disease; lichen simplex chronicus; keratoses; acne; pseudofolliculitis barbae; eczema; psoriasis; itchy scalp and skin; pruritus; warts; herpes; age spots; lentigines; melasmas; blemished skin; hyperkeratoses; hyperpigmented skin; abnormal or diminished syntheses of collagen, glycosaminoglycans, proteoglycans and elastin as well as diminished levels of such components in the dermis; stretch marks; skin lines; fine lines; wrinkles; thinning of skin, nail plate and hair, skin thickening due to elastosis of photoaging, loss or reduction of skin, nail and hair resiliency, elasticity and recoilability; lack of skin, nail and hair lubricants and luster; dull and older-looking skin, nail and hair; and fragility and splitting of nail and hair.

13. The method of claim 12, wherein said composition further comprises a cosmetic, pharmaceutical, or other topical agent.

14. The method of claim 13, wherein said cosmetic, pharmaceutical, or other topical agent is selected from the group consisting of agents that improve or eradicate age spots, keratoses and wrinkles; local analgesics and anesthetics; antiacne agents; antibacterials; antiyeast agents; antifungal agents; antiviral agents; antidandruff agents; antidermatitis agents; antihistamine agents; antipruritic agents; antiemetics; antimotion sickness agents; antiinflammatory agents; antihyperkeratolytic agents; antiperspirants; antipsoriatic agents; antiseborrheic agents; hair conditioners and hair treatment agents; antiaging and antiwrinkle agents; sunblock and sunscreen agents; skin lightening agents; depigmenting agents; vitamins; corticosteroids; tanning agents; hormones; amino acids; dipeptides; tripeptides; oligopeptides; polypeptides; retinoids; topical cardiovascular agents; hydroxyacids, ketoacids and related compounds; phenyl alpha acyloxyalkanoic acids and derivatives thereof; and N-acetyl-aldosamines, N-acetylamino acids and related N-acetyl compounds.

15. The method of claim 14, wherein said cosmetic, pharmaceutical, or other topical agent is selected from the group consisting of aclovate, acyclovir, acetylsalicylic acid, adapalene, albuterol, aluminum acetate, aluminum chloride, aluminum hydroxide, aluminum chlorohydroxide, amantadine, aminacrine, aminobenzoic acid (PABA), γ-aminobutanoic acid, aminocaproic acid, aminosalicylic acid, amitriptyline, anserine, anthralin, ascorbic acid, ascoryl palimate, atropine, azelaic acid, bacitracin, bemegride, beclomethasone dipropionate, benzocaine, benzophenone, benzoyl peroxide, betamethasone dipropionate, betametbasone valerate, brompheniramine, bupivacaine, butoconazole, calcipotriene, camphor, capsaicin, carbamide peroxide, carnosine, chitosan, chlorhexidine, chloroxylenol, chlorpheniramine, ciclopirox, clemastine, clindamycin, clioquinol, clobetasol propionate, clotrimazole, coal tar, cromolyn, crotamiton, cycloserine, dehydroepiandrosterone, desoximetasone, dexamethasone, diphenhydramine, doxypin, doxylamine, dyclonine, econazole, erythromycin, estradiol, ethinyl estradiol, fluocinonide, fluocinolone acetonide, 5-fluorouracil, glutathione, griseofulvin, guaifenesin, haloprogin, hexylresorcinol, homocarnosine, homosalate, hydrocortisone, hydrocortisone 21-acetate, hydrocortisone 17-valerate, hydrocortisone 17-butyrate, hydrogen peroxide, hydroquinone, hydroquinone monoether, hydroxyzine, ibuprofen, ichthammol, imiquimod, indomethacin, ketoconazole, ketoprofen, kojic acid, lidocaine, meclizine, meclocycline, menthol, mepivacaine, methyl nicotinate, methyl salicylate, metronidazole, miconazole, minacycline, minoxidil, monobenzone, mupirocin, naftifine, naproxen, neomycin, nystatin, octyl methoxycinnamate, octyl salicylate, ophidine, ornithine, oxybenzone, oxiconazole, oxymetazoline, padimate O, permethrin, pheniramine, phenol, phenylephrine, phenylpropanolamine, piperonyl butoxide, podophyllin, podofilox, povidone iodine, polymyxins, pramoxine, prilocaine, procaine, promethazine propionate, propranolol, pseudoephedrine, pyrethrin, pyrilamine, resorcinol, retinal, 13-cis retinoic acid, retinoic acid, retinol, retinyl acetate, retinyl palmitate, salicylamide, salicylic acid, selenium sulfide, shale tar, sulconazole, sulfur, sulfadiazine, tazarotene, terbinafine, terconazole, tetracaine, tetracycline, tetrahydrozoline, thymol, tioconazole, tolnaftate, triamcinolone diacetate, triamcinolone acetonide, triamcinolone hexacetonide, triclosan, triprolidine, undecylenic acid, urea, vitamin E acetate, wood tar, zinc pyrithione, glycolic acid, lactic acid, methyllactic acid, 4-hydroxy-mandelic acid, mandelic acid, gluconolactone, N-acetyl-glucosamine, N-acetyl-proline, phenyl 2-acetoxyethanoic acid and diphenyl 2-acetoxyethanoic acid.

16. The method of claim 12, wherein said composition further comprises an inorganic or organic alkali, or amphoteric substance.

17. The method of claim 16, wherein said inorganic alkali is selected from the group consisting of ammonium hydroxide, ammonium phosphate, ammonium carbonate, ammonium bicarbonate, sodium hydroxide, sodium carbonate, sodium bicarbonate, sodium acetate, sodium phosphate, and alkalis formed from potassium, calcium, magnesium, strontium, aluminum, zinc, and lithium.

18. The method of claim 16, wherein said organic alkali is selected from the group consisting of amines, hydroxylamines, imines, guanidines, amine oxides, alkanolamines, alkoxylated amines, alkylamido alkylamines, organic amines, polyamines, hydroxylamines, amino acid esters, amino acid amides, aminosaccharides, aminoalditols, aminocyclitols, fattyamines, and imidazolines.

19. The method of claim 16, wherein said organic alkali is selected from the group consisting of diethanolamine, triethanolamine, isopropanolamine, diisopropanolamine, trilsopropanolamine, aminobutanol, aminoethyl propanediol, aminomethyl propanol, aminomethyl propanediol, isopropylamine, dimethylaminoethanol, diethylaminoethanol, methylethanolamine, diisopropylamine, dipropylenetriamine, glucamine, N-methylglucamine, morpholine, trometharmine, cocamines, soyamines, oleamines, stearamines, quaterniums, creatinine, glycine ethyl ester, arginine ethyl ester, lysine methyl ester, proline ethyl ester, citrulline benzyl ester, glycinamide, argininarmide, prolinamide, lysinamide, glucamine, methylglucamine, glucosamines and glucosylamines, other glycosamines and glycosylamines, aminoinositols, chitosan, stearamidoethyl diethylamine, stearamidopropyl dimethylamine, stearamidoethyl diethanolamine, and quaternary ammonium hydroxide.

20. The method of claim 16, wherein said amphoteric substance is selected from the group consisting of amino acids, peptides, polypeptides, proteins and related compounds.

21. The method of claim 16, wherein said amphoteric substance is selected from the group consisting of glycine, arginine, lysine, cysteine, proline, glutamine, histidine, asparagine, tyrosine, ornithine, citrulline, creatine, creatinine, and tryptophan.

22. A method for general care or treatment or prevention of diseases or conditions of the oral, vaginal or anal mucosa or for treating skin wounds, comprising topically applying a composition comprising (A) a topically acceptable vehicle or base and (B) a therapeutically effective amount of at least one compound selected from the group consisting of lactobiomc acid, isolactobionic acid, maltobionic acid, isomaltobionic acid, cellobionic acid, gentiobionic acid, laminarabionic acid, melibionic acid, nigerobionic acid, rutinobionic acid, sophorobionic acid, and kojibionic acid as isomeric, nonisomeric, free acid, ester, salt, partial salt, lactone, saturated or unsaturated, straight or branched chain, or cyclic form thereof.

23. The method of claim 22, wherein said skin wounds are selected from the group consisting of skin cuts, tears, lacerations, burns, and punctures.

24. The method of claim 22, wherein said composition further comprises a cosmetic, pharmaceutical, or other topical agent.

25. The method of claim 24, wherein said cosmetic, pharmaceutical, or other topical agent is selected from the group consisting of local analgesics and anesthetics; antibacterials; antiyeast agents; antifungal agents; antiviral agents; antidermatitis agents; antihistamine agents; antipruritic agents; antiinflammatory agents; vitamins; corticosteroids; hormones; retinoids; N-acetyl-aldosamines, N-acetylamino acids and related N-acetyl compounds.

26. The method of claim 25, wherein said cosmetic, pharmaceutical, or other topical agent is selected from the group consisting of benzocaine, clotrimazole, ketoconazole, miconazole, griseofulvin, econazole, metronidazole, hydroxyzine, diphenhydramine, phenylephrine, pramoxine, lidocaine, procaine, mepivacaine, erythromycin, tetracycline, clindamiycin, meclocycline, minocycline, naproxen, ibuprofen, theophylline, cromolyn, albuterol, retinol, retinyl acetate, retinyl palinitate, retinal, retinoic acid, 13-cis retinoic acid, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol, propionate, crotamiton, propranolol, promethazine, salicylic acid, vitamin E, vitamin E acetate, mandelic acid, gluconolactone, N-acetyl-glucosamine, N-acetyl-proline.

27. A method of using lactobionic acid as isomeric, nonisomeric, free acid, ester, salt, partial salt, lactone, saturated or unsaturated, straight or branched chain, or cyclic form thereof, for general care or treatment of skin and nail, and for topical treatment or prevention of cosmetic conditions or dermatological disorders selected from the indications consisting of dryness or looseness of skin, nail and hair; xerosis; ichthyosis; palmar and plantar hyperkeratoses; uneven and rough surface of skin, nail and hair; dandruff; Darier's disease; lichen simplex chronicus; keratoses; acne; pseudofolliculitis barbae; eczema; psoriasis; pruritus; warts; herpes; age spots; lentigines; melasmas; blemished skin; mottled skin; hyperkeratoses; hyperpigmented skin; stretch marks; thinning of nail plate and hair; fragility and splitting of nail and hair; wound-healing and treatment of skin wounds; general care as well as treatment and prevention of diseases and conditions of oral, gum, vaginal and anal mucosa.

28. The method of claim 27, further comprising a cosmetic, pharmaceutical, or other topical agent selected from the group consisting of local analgesics and anesthetics; antibacterials; antiyeast agents; antifungal agents; antiviral agents; antidandruff agents; antidermatitis agents; antihistamine agents; ancipruritic agents; antiemetics; antimotion sickness agents; antiinflammatory agents; antihyperkeratolytic agents; antiperspirants; antipsoriatic agents; antiseborrheic agents; vitamins; corticosteroids; tanning agents; hormones; amino acids; dipeptides; tripeptides; oligopeptides; polypeptides; retinoids; wound healing agents; oral, vaginal and anal care or treatment agents; gum disease treatment or care agents; hydroxyacids, ketoacids and related compounds; phenyl alpha acyloxyalkanoic acids and derivatives thereof; and N-acetyl-aldosamines, N-acetylamino acids and related N-acetyl compounds.

29. The method of claim 28, wherein said cosmetic, pharmaceutical, or other topical agent is selected from the group consisting of aclovate, acyclovir, adapalene, albuterol, aluminum acetate, aluminum chloride, aluminum hydroxide, aluminum chiorohydroxide, amantadine, aminacrine, aminobenzoic acid (PABA), γ-aminobutanoic acid, aminocaproic acid, aminosalicylic acid, amitriptyline, anserine, anthralin, ascorbic acid, ascoryl palimate, atropine, azelaic acid, bacitracin, bemegride, beclomethasone dipropionate, benzocaine, betamethasone dipropionate, betamethasone valerate, brompheniramine, bupivacaine, butoconazole, calcipotriene, camphor, capsaicin, carbamide peroxide, carnosine, chitosan, chiorhexidine, chloroxylenol, chiorpheniramine, ciclopirox, clemastine, clindamycin, clioquinol, clobetasol propionate, clotrimazole, coal tar, cromolyn, crotamiton, cycloserine, dehydroepiandroscerone, desoximetasone, dexamethasone, diphenhydramine, doxypin, doxylamine, dyclonine, econazole, erythromycin, estradiol, ethinyl estradiol, fluocinonide, fluocinolone acetonide, 5-fluorouracil, glutathione, griseofulvin, guaifenesin, haloprogin, hexylresorcinol, homocarnosine, homosalate, hydrocortisone, hydrocortisone 21-acetate, hydrocortisone 17-valerate, hydrocortisone 17-butyrate, hydrogen peroxide, hydroxyzine, ibuprofen, ichthammol, imiquimod, indomethacin, ketoconazole, ketoprofen, lidocaine, meclizine, meclocycline, menthol, mepivacaine, methyl nicotinate, methyl salicylate, metronidazole, miconazole, minocycine, minoxidil, mupirocin, naftifine, naproxen, neomycin, nystatin, ophidine, ornithine, oxiconazole, oxymetazoline, permethrin, pheniramine, phenol, phenylephrine, phenylpropanolazmine, piperonyl butoxide, podophyllin, podofilox, povidone iodine, polymyxins, pramoxine, prilocaine, procaine, promethazine propionate, propranolol, pseudoephedrine, pyrethrin, pyrilamine, resorcinol, retinol, retinyl acetate, retinyl palmitate, salicylamide, selenium sulfide, shale tar, sulconazole, sulfur, sulfadiazine, tazarotene, terbinafine, terconazole, tetracaine, tetracycline, tetrahydrozoline, thymol, tioconazole, tolnaftate, triamcinolone diacetate, triamcinolone acetonide, triamcinolone hexacetonide, triclosan, triprolidine, undecylenic acid, urea, vitamin E acetate, wood tar, zinc pyrithione, glycolic acid, lactic acid, methyllactic acid, 4-hydroxy-mandelic acid, mandelic acid, gluconolactone, N-acetyl-glucosamine, N-acetyl-proline, phenyl 2-acetoxyethanoic acid and diphenyl 2-acetoxyethanoic acid.

30. The method of claim 27, wherein the general care or treatment is for prevention and/or treatment against stinging or irritations of skin caused by chemicals, procedures or other means.

31. A method of forming a gel matrix on the skin, hair, nail or mucosa for the purpose of protection and other attributes comprising at least one compound selected from the group consisting of lactobionic acid, isolactobionic acid, maltobionic acid, isomaltobionic acid, cellobionic acid, gentiobionic acid, laminarabionic acid, melibionic acid, nigerobionic acid, rutinobionic acid, sophorobionic acid, and kojibionic acid as isomeric, nonisomeric, free acid, ester, salt, partial salt, lactone, saturated or unsaturated, straight or branched chain, or cyclic form thereof.

32. An antioxidant comprising (A) an acceptable vehicle or base and (B) a therapeutically effective amount of at least one compound selected from the group consisting of lactobionic acid, isolactobionic acid, maltobionic acid, isomaltobionic acid, cellobionic acid, gentiobionic acid, laminarabionic acid, melibionic acid, nigerobionic acid, rutinobionic acid, sophorobionic acid, and kojibionic acid asisomeric, nonisomeric, free acid, ester, salt, partial salt, lactone, saturated or unsaturated, straight or branched chain, or cyclic form thereof.

33. The antioxidant of claim 32, wherein the antioxidant is used for the prevention and/or treatment against damage from radiation, ionizing radiation, free radicals, laser, or other oxidative damages to the skin, hair, and nails.

34. A compound selected from the group consisting of isolactobionic acid, maltobionic acid, isomaltobionic acid, cellobionic acid, gentiobionic acid, laminarabionic acid, melibionic acid, nigerobionic acid, rutinobionic acid, sophorobionic acid, and kojibionic acid as isomeric, nonisomeric, free acid, ester, salt, partial salt, lactone, saturated or unsaturated, and straight or branched chain, or cyclic forms thereof.

35. The method of claim 27, wherein the general care or treatment is for prevention and/or treatment against stinging or irritations of skin caused by chemicals, procedures or other means.

36. A composition comprising maltobionic acid in an acceptable vehicle or base.

37. The composition of claim 36, wherein maltobionic acid is present as free acid, ester, salt, partial salt, lactone, isomeric or nonisomeric, saturated or unsaturated, straight or branched chain, or cyclic forms thereof.

38. The composition of claim 36, comprising a cosmetic, pharmaceutical, or other topical agent.

39. A composition comprising melibionic acid in an acceptable vehicle or base.

40. The composition of claim 39, wherein melibionic acid is present as free acid, ester, salt, partial salt, lactone, isomeric or nonisomeric, saturated or unsaturated, straight or branched chain, or cyclic forms thereof.

41. The composition of claim 40, further comprising a cosmetic, pharmaceutical, or other topical agent.

42. A method of using lactobionic acid, its free acid, ester, salt, partial salt, lactone, saturated or unsaturated, isomeric or nonisomeric, straight or branched chain, or cyclic form thereof, as skin refinisher; to improve skin pores, flakiness and redness; to make skin soft, smooth, fresh, balanced, visibly clear, even-toned and brighter.

43. A method of using maltobionic acid, its free acid, ester, salt, partial salt, lactone, saturated or unsaturated, isomeric or nonisomeric, straight or branched chain, or cyclic form thereof, as skin refinisher; to improve skin pores, flakiness and redness; to make skin soft, smooth, fresh, balanced, visibly clear, even-toned and brighter.

44. A method of using lactobionic acid, its free acid, ester, salt, partial salt, lactone, saturated or unsaturated, isomeric or nonisomeric, straight or branched chain, or cyclic form thereof, as preventive care or treatment for damages caused by laser treatment or procedure, electromagnetic radiation or ionizing radiation such as alpha rays, beta rays, X-rays and gamma rays.

45. A method of using maltobionic acid, its free acid, ester, salt, partial salt, lactone, saturated or unsaturated, isomeric or nonisomeric, straight or branched chain, or cyclic form thereof, as preventive care or treatment for damages caused by laser treatment or procedure, electromagnetic radiation or ionizing radiation such as alpha rays, beta rays, X-rays and gamma rays.

46. A topical cosmetic composition comprising lactobionic acid or maltobionic acid, and N-acetyl-glucosaniine, present as free acid, ester, salt, partial salt, lactone, saturated or unsaturated, isoineric or nonisomeric, straight or branched chain or cyclic form thereof.

47. A topical cosmetic composition comprising lactobionic acid or maltobionic acid, and polybydroxy acids selected from the group consisiting of ribonolactone, gluconolactone, galactonolactone, glucoheptonolactone, glucuronolactone, galacturonolactone, glucarolactone and galactarolactone, wherein the bionic acids and polyhydroxy acids may be present as free acid, ester, salt, partial salt, lactone, saturated or unsaturated, isomeric or nonisomeric, straight or branched chain or cyclic form thereof.

48. A topical cosmetic composition comprising lactobiomc acid or maltobionic acid, and ascorbic acid present as free acid, ester, salt, partial salt, lactone, saturated or unsaturated, isomeric or nonisomeric, straight or branched chain or cyclic form thereof.

\* \* \* \* \*